(12) United States Patent
Lyerly et al.

(10) Patent No.: US 12,083,172 B2
(45) Date of Patent: Sep. 10, 2024

(54) VACCINES AGAINST AN ONCOGENIC ISOFORM OF HER2 (ErbB2) AND METHODS OF USING THE SAME

(71) Applicant: Duke University, Durham, NC (US)

(72) Inventors: Herbert K. Lyerly, Durham, NC (US); Takuya Osada, Durham, NC (US); Zachary C. Hartman, Durham, NC (US)

(73) Assignee: Duke University, Durham, NC (US)

( * ) Notice: Subject to any disclaimer, the term of this patent is extended or adjusted under 35 U.S.C. 154(b) by 463 days.

(21) Appl. No.: 16/953,221

(22) Filed: Nov. 19, 2020

(65) Prior Publication Data

US 2021/0077606 A1    Mar. 18, 2021

Related U.S. Application Data

(60) Continuation of application No. 16/045,248, filed on Jul. 25, 2018, now Pat. No. 10,842,857, which is a division of application No. 15/324,215, filed as application No. PCT/US2015/039359 on Jul. 7, 2015, now abandoned.

(60) Provisional application No. 62/021,554, filed on Jul. 7, 2014.

(51) Int. Cl.
| | |
|---|---|
| *A61K 39/00* | (2006.01) |
| *A61K 38/45* | (2006.01) |
| *A61K 39/395* | (2006.01) |
| *C07H 21/04* | (2006.01) |
| *C07K 16/28* | (2006.01) |
| *C12N 7/00* | (2006.01) |

(52) U.S. Cl.
CPC ...... *A61K 39/001106* (2018.08); *A61K 38/45* (2013.01); *A61K 39/001102* (2018.08); *A61K 39/001104* (2018.08); *A61K 39/3955* (2013.01); *C07H 21/04* (2013.01); *C07K 16/2818* (2013.01); *C12N 7/00* (2013.01); *C12Y 207/10001* (2013.01); *A61K 2039/53* (2013.01); *C07K 2317/76* (2013.01); *C12N 2740/15034* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 6,734,172 B2 * | 5/2004 | Scholler | C07K 14/705 435/320.1 |
| 7,737,253 B2 | 6/2010 | Robins | |
| 8,445,268 B2 | 5/2013 | Lee et al. | |
| 8,846,080 B2 | 9/2014 | Biemans et al. | |
| 9,062,096 B2 | 6/2015 | Ling | |
| 9,216,229 B2 | 12/2015 | Brown et al. | |
| 9,226,959 B2 | 1/2016 | Kramps et al. | |
| 9,630,993 B2 | 4/2017 | Ling | |
| 9,884,918 B2 | 2/2018 | Ling | |
| 9,956,276 B2 | 5/2018 | Lyerly | |
| 2003/0143568 A1 | 7/2003 | Singer et al. | |
| 2003/0228606 A1 | 12/2003 | Tatarewicz et al. | |
| 2003/0232350 A1 | 12/2003 | Afar et al. | |
| 2004/0253606 A1 | 12/2004 | Aziz et al. | |
| 2005/0266409 A1 | 12/2005 | Brown et al. | |
| 2008/0057064 A1 | 3/2008 | Zhou | |
| 2009/0214518 A1 | 8/2009 | Buckanovich et al. | |
| 2010/0055093 A1 | 3/2010 | Shepard et al. | |
| 2010/0279399 A1 | 11/2010 | Robins et al. | |
| 2010/0310640 A1 * | 12/2010 | Knutson | C07K 14/70503 530/331 |
| 2011/0281748 A1 | 11/2011 | Singh et al. | |
| 2012/0014984 A1 | 1/2012 | Shahabi | |
| 2014/0017259 A1 | 1/2014 | Aurisicchio et al. | |
| 2014/0221329 A1 | 8/2014 | Cronin et al. | |
| 2014/0377261 A1 | 12/2014 | Lyerly | |
| 2015/0047065 A1 | 2/2015 | Brack et al. | |
| 2015/0258099 A1 | 9/2015 | Hager et al. | |
| 2018/0092989 A1 | 4/2018 | Lyerly et al. | |
| 2018/0094050 A1 | 4/2018 | Lyerly et al. | |
| 2018/0282736 A1 | 10/2018 | Lyerly et al. | |

FOREIGN PATENT DOCUMENTS

| | | |
|---|---|---|
| WO | 2008/049930 | 5/2008 |
| WO | 2011060260 | 5/2011 |
| WO | 2011146568 | 11/2011 |

(Continued)

OTHER PUBLICATIONS

Mukai et al (Gene Therapy, 2002, 9:879-888).*
Chen et al (Cancer Gene Therapy, 2011, 18:489-499).*
Yamamoto et al (Nature, 1986, 319:230-234).*
Orlandi et al (Vaccine, 2011, 29:3646-3654).*
Norell et al (Journal of Translational Medicine, 2010, 8:53, internet pp. 1-7).*
Castiglioni et al (Endocrine-Related Cancer, 2006; 13:221-232).*
Mitra et al (Molecular Cancer Therapeutics, 2009, 8:2152-2162).*
Lee CH, et al. Assessment of Her-1, Her-2, And Her-3 expression and Her-2 amplification in advanced stage ovarian carcinoma. Int J Gynecol Pathol. 2005;24(2):147-52.

(Continued)

*Primary Examiner* — Laura B Goddard
(74) *Attorney, Agent, or Firm* — Quarles & Brady, LLP

(57) ABSTRACT

Methods of reducing the likelihood of a cancer or precancer developing resistance to a cancer therapeutic or prevention agent are provided herein. The methods include administering a vaccine comprising a polynucleotide encoding a polypeptide whose expression or activation is correlated with development of resistance of the cancer or precancer to the cancer therapeutic or prevention agent to a subject. The vaccine may include a polynucleotide encoding a HER2 polypeptide or a truncation, deletion or substitution mutant thereof. Methods of using the vaccine including the polynucleotide encoding the HER2 polypeptide to treat a cancer or precancer are also provided. The vaccines may be administered with a cancer therapeutic or prevention agent or a checkpoint inhibitor immunomodulatory agent.

12 Claims, 14 Drawing Sheets

Specification includes a Sequence Listing.

(56) References Cited

FOREIGN PATENT DOCUMENTS

| WO | 2011154863 | 12/2011 |
|---|---|---|
| WO | 2012125864 | 9/2012 |
| WO | 2013110030 | 7/2013 |
| WO | 2016007504 | 1/2016 |
| WO | 2017120576 | 7/2017 |

OTHER PUBLICATIONS

Lee-Hoeflich, ST et al. "A central role for HER3 in HER2-amplified breast cancer: implications for targeted therapy." (2008) Cancer Res 68:5878-87.

Leonard, JP et al. "Effects of single-dose interleukin-12 exposure on interleukin-12-associated toxicity and interferon-y production." (1997) Blood 90:2541-8.

Li, B. et al. Anti-programmed death-1 synergizes with granulocyte macrophage colony-stimulating factor-secreting tumor cell immunotherapy providing therapeutic benefit to mice with established tumors. Clin Cancer Res. 2009;15(5):1623-34.

Liddy et al., Monoclonal TCR-redirected tumor cell killing. Nature Med. 18:980-7 (2012).

Liu, B et al. Downregulation of erbB3 abrogates erbB2-mediated tamoxifen resistance in breast cancer cells. (2007) Int J Cancer 120:1874-82.

Luo, et al. "A protocol for rapid generation of recombinant adenoviruses using the AdEasy system" (2007) Nature Protocols 2:1236.

Makhija, S et al. "clinical activity of gemcitabine plus pertuzumab in platinum-resistant ovarian cancer, fallopian tube cancer, or primary peritoneal cancer." (2010) J Clin Oncol 28:1215-23.

Miller, T.W. et al. "Loss of Phosphatase and Tensin homologue deleted on chromosome 10 enages ErbB3 and Insulin-like growth factor-I receptor signaling to promote antiestrogen resistance in breast cancer." (2009) Cancer Res 69:4192-201.

Mitra, D. "An oncogenic isoform of HER2 associated with locally disseminated breast cancer and trastuzumab resistance" (2009) Mol Cancer Ther 8(8): 2152-2162.

Morse, MA et al. Synergism from combined immunologic and pharmacologic inhibition of HER2 in vivo. (2010) Int J Cancer 126:2893-903.

Nabholtz, J.M. et al., "Anastrozole is superior to tamoxifen as first-line therapy for advanced breast cancer in postmenopausal women: results of a North American multicenter randomized trial. Arimidex Study Group" (2000) J Clin Oncol 18(22): 3758-3767.

Nanda R, et al. Pembrolizumab in Patients With Advanced Triple-Negative Breast Cancer: Phase lb Keynote-012 Study. J Clin Oncol. 2016;34(21):2460-7.

Norell, H. et al "Vaccination with a plasmid DNA encoding HER-2/neu together with low doses of GM-CSF and IL-2 in patients with metastatic breast carcinoma: a pilot clinical trial" J. Transl. Med. 2010. 8:53.

O'Neil, LA et al. "Therapeutic targeting of toll-like receptors for infectious and inflammatory diseases and cnacer." (2009) Pharmacol Rev 61:177-97.

Ono, Y. et al., "Phorbol ester binding to protein kinase C requires a cysteine-rich zinc-finger-like sequence" (1989) Proc. Natl. Acad. Sci. USA 86:4856-4871.

Osada T, et al. Optimization of vaccine responses with an E1, E2b and E3-deleted Ad5 vector circumvents pre-existing anti-vector immunity. Cancer Gene Ther. 2009; 16(9):673-82.

Osada, T et al. "Vaccination targeting human HER3 alters the phenotype of infiltrating T cells and respones to immune checkpoint inhibition." (2017). OncoImmunology 0(0).

Osipo, C et al. "Role for HER2/neu and HER3 in fulvestrant-resistant breast cancer." (2007) Int J Oncol 30:509-20.

Pederson, MW et al. "Sym004: a novel synergistic anti-epidermal growth factor receptor antibody mixture with superior anticancer efficacy." (2010) Cancer Res 70:588-97.

Pulaski, BA et al. "Reduction of established spontaneous mammary carcinoma metastases following immunotherapy with major histocompatibility complex class II and B7.1 cell-based tumor vaccines." (1998) Cancer Res. 58:1486-93.

Ren et al. "Polyclonal Her2-specific antibodies induced by vaccination mediate receptor internalization and degradation in tumor cells" (2012) Breast cancer research 14: R89.

Renard, V. et al., "HER-2 DNA and Protein Vaccines Containing Potent Th Cell Epitopes Induce Distinct Protective and Therapeutic Antitumor Responses in HER-2 Transgenic Mice" (2003) J Immunol 171(3): 1588-1595.

Rosenberg, SA et al., Adoptive cell transfer: a clinical path to effective cancer immunotherapy. Nat. Rev. Cancer 8 (4): 299-308 (2008).

Roskoski R, Jr. The ErbB/HER family of protein-tyrosine kinases and cancer. Pharmacological research : the official journal of the Italian Pharmacological Society. 2014;79:34-74.

Sakai K, et al. Pertuzumab, a novel HER dimerization inhibitor, inhibits the growth of human lung cancer cells mediated by the HER3 signaling pathway. Cancer Sci. 2007;98(9):1498-503.

Schoeberl, B. et al. "An ErbB3 Antibody, MM-121, Is Active in Cancers with Ligand-Dependent Activation" (2010) Cancer Research: 70(6): 2485-2494.

Sergina, NV et al. "Escape from HER-family tyrosine kinase inhibitor therapy by the kinase-inactive HER3." (2007) Nature 445:437-41.

Soares KC, et al. PD-1/PD-L1 blockade together with vaccine therapy facilitates effector T-cell infiltration into pancreatic tumors. J Immunother. 2015;38(1):1-11.

Takikita M, et al. Membranous expression of Her3 is associated with a decreased survival in head and neck squamous cell carcinoma. J Transl Med. 2011;9:126.

Tanaka, T. et al., "Efficient generation of antibodies to oncoproteins by using synthetic peptide antigens," (1985) Proc. Natl. Acad. Sci. USA 82:3400-3404.

Tiriveedhi V, et al. Safety and preliminary evidence of biologic efficacy of a mammaglobin-a DNA vaccine in patients with stable metastatic breast cancer. Clinical cancer research : an official journal of the American Association for Cancer Research. 2014;20(23):5964-75.

Topalian SL, et al. Immune checkpoint blockade: a common denominator approach to cancer therapy. Cancer Cell. 2015;27(4):450-61.

Tovey S, et al. Can molecular markers predict when to implement treatment with aromatase inhibitors in invasive breast cancer? Clin Cancer Res. 2005;11(13):4835-42.

Van Elsas A, et al. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. 1999;190(3):355-66.

Xia W, et al. An heregulin-EGFR-HER3 autocrine signaling axis can mediate acquired lapatinib resistance in HER2+ breast cancer models. Breast cancer research : BCR. 2013;15(5):R85.

Xia, W. et al. "A model of acquired autoresistance to a potent ErbB2 tyrosine kinase inhibitor and a therapeutic strategy to prevent its onset in breast cancer." (2006) 103:7795-800.

Yamamoto, T. et al. "Similarity of protein encoded by the human c-erb-B-2 gene to epidermal growth factor receptor" Nature. 1986. 319(605):230-234.

Yoo, J.Y. et al., "Downregulation of ErbB3 Expression by Adenovirus Expressing ErbB3 Specific shRNA Enhances Antitumor Efficacy through Apoptosis Induction" (2009) Molecular Therapy: 17(Suppl. 1): S106.

Yu, P et al. "Targeting the primary tumor to generate CTL for the effective eradication of spontaneous metastases." (2007) J Immunol 179:1960-8.

Yuan, J. et al., "CTLA-4 blockade increases antigen-specific CD8(+) T cells in prevaccinated patients with melanoma: three cases" (2011) Cancer Immunol Immunother, 60(8): 1137-1146.

Zitvogel, L et al. "The anticancer immune response: indispensable for therapeutic success?" (2008) 118:1991-2001.

(56) References Cited

OTHER PUBLICATIONS

International Search Report and Written Opinion for PCT/US2015/039359 mailed Oct. 7, 2015 (15 pages).
Office Action for U.S. Appl. No. 15/324,215 12 mailed Dec. 27, 2017 (12 pages).
Office Action for U.S. Appl. No. 15/324,215 mailed Apr. 25, 2018 (14 pages).
Abd El-Rehim, DM et al. "Expression and co-expression of the members of the epidermal growth factor receptor (EGFR) family in invasive breast carcinoma." (2004) Br J Cancer 91:1532-42.
Agus, DB et al. "Targeting ligand-activiated ErbB2 signaling inhibits breast and prostate tumor growth." (2002) 2:127-37.
Alimandi M et al. "Cooperative signaling of ErbB3 and ErbB2 in neoplastic transformation and human mammary carcinomas." (1995) Oncogene 10:1813-21.
Amalfitano A, et al. Production and characterization of improved adenovirus vectors with the E1, E2b, and E3 genes deleted. J Virol. 1998;72(2):926-33.
Amin, DN et al. "Resiliency and vulnerability in the HER2-HER3 tumorigenic driver." (2010) Sci Transl Med 2:16-17.
Arteaga et al. Treatment of HER2-positive breast cancer: current status and future perspectives. Nature Reviews Clinical Oncology, 9: 16-32, 2012.
Atkins, MB et al. "Phase I evaluation of intravenous recombinant human interleukin 12 in patients with advanced malignancies." (1997) Clin Cancer Res 3:409-17.
Begnami MD, et al. Prognostic implications of altered human epidermal growth factor receptors (HERs) in gastric carcinomas: HER2 and HER3 are predictors of poor outcome. J Clin Oncol. 2011;29(22):3030-6.
Ben-Kasus, T. et al. "Persistent elimination of ErbB-2/HER2-overexpressing tumors using combinations of monoclonal antibodies: relevance of receptor endocytosis." (2009) Proc Natl Acad Sci USA 106:3294-99.
Binder DC, et al. Antigen-specific bacterial vaccine combined with anti-PD-L1 rescues dysfunctional endogenous T cells to reject long-established cancer. Cancer immunology research. 2013;1(2):123-33.
Blattman, JN et al. "Cancerimmunotherapy: a treatment for the masses." (2004) Science 305:200-5.
Cai Z, et al. Targeting erbB receptors. Seminars in cell & developmental biology. 2010;21(9):961-6.
Cai, Z et al. "Differential binding patterns of monoclonal antibody 2C4 to the ErbB3-p185her2/neu and the EGFR-p185her2/neu complexes." (2008) 27:3870-4.
Campbell, MR et al. "HER3 comes of age: new insights into its functions and role in signaling, tumor biology, and cancer therapy." Clin cancer Res (2010) 16:1373-83.
Castagnoli, L. et al., "Activated d16HER2 homodimers and SRC kinase mediate optimal efficacy for trastuzumab" (2014) Cancer Res 74(21): 6248-6259.
Castiglioni et al. Role of exon-16-deleted HER2 in breast carcinomas. (2006) Endocr Relat Cancer: 13(1):221-232.
Clay, T. et al., "Polyclonal Immune Responses To Antigens Associated With Cancer Signaling Pathways And New Strategies To Enhance Cancer Vaccines" (2011) Immunolo Res 49(0): 235-247.
Drake, CG et al. Mechanisms of immune evasion by tumors. (2006) Adv Immunol 90:51-81.
Dranoff, G. "Cytokines in cancer pathogenesis and cancer therapy." (2004) Nat Rev Cancer 4:11-22.
Eager, R et al. "GM-CSFF gene-transduced tumor vaccines." (2005) Mol Ther. 12:18-27.
Ebctcg, et al., "Relevance of breast cancer hormone receptors and other factors to the efficacy of adjuvant tamoxifen: patient-level meta-analysis of randomised trials" (2011) Lancet 378(9793): 771-784.
Erjala, K et al. "Signaling via ErbB2 and ErbB3 associates with resistance and epidermal growth factor receptor (EGFR) amplication with sensitivity to EGRF inhibitor gefitnib in head and neck squamous cell carcinoma cells." (2006) Clin Cancer Res 12:4103-11.
Fourcade J, et al. PD-1 and Tim-3 regulate the expansion of tumor antigen-specific CD8(+) T cells induced by melanoma vaccines. Cancer Res. 2014;74(4):1045-55.
Friedman, LM et al. "Synergistic down-regulation of receptor tyrosine kinase by combinations of mAbs: implications for cancer immunotherapy." (2005) Proc Natl Acad Sci USA 102:1915-20.
Fu, J. et al., "Preclinical evidence that PD1 blockade cooperates with cancer vaccine TEGVAX to elicit regression of established tumors" (2014) Cancer Res, 74(15): 4042-4052.
Gala K, et al. Molecular pathways: HER3 targeted therapy. Clin Cancer Res. 2014;20(6):1410-6.
Gallo, P. et al., "Xenogenic Immunization in Mice Using HER2 DNA Delivered by an Adenoviral Vector" (2005) Int. J. Cancer 113(1): 67-77.
Giltnane JM, et al. Quantitative multiplexed analysis of ErbB family coexpression for primary breast cancer prognosis in a large retrospective cohort. Cancer. 2009;115(11):2400-9.
Goldman, B et al. "The cancer vaccine roller coaster." (2009) Nat Biotechnol 27:129-39.
Greenspan, N.S. et al., "Defining epitopes: It's not as easy as it seems," (1999) Nature Biotechnology 7:936-937.
Grupp et al., Chimeric antigen receptor-modified T cells for acute lymphoid leukemia. New England J. Med. 368:1509-18, (2013).
Hartman, Z. et al. "HER2 overexpression elicits a proinflammatory IL-6 autocrine signaling loop that is critical for tumorigenesis" (2011) Cancer Res 71(13): 4380-4391.
Hartman, Z. et al., "An Adenoviral vaccine encoding full-length inactivated human Her2 exhibits potent immunogenicity and enhanced therapeutic efficacy without oncogenicity" (2010) Clin Cancer Res 16(5): 1466-1477.
Hartman, Z. et al., "Growth of triple-negative breast cancer cells relies upon coordinate autocrine expression of the proinflammatory cytokines IL-6 and IL-8" (2013) Cancer Res 73(11): 3470-3480.
Hartman, Z. et al., "Ligand-independent TLR signals generated by ectopic overexpression of MyD88 generate local and systemic anti-tumor immunity" (2010) Cancer Res 70(18): 7209-7220.
Hartman, Z. et al., Increasing vaccine potency through exosome antigen targeting. Vaccine. Nov. 21, 2011;29(50):9361-7.
He, TC et al. "A simplified system for generating recombinant adenoviruses." (1998) Proc Natl Acad Sci USA 95:2509-14.
Hodges, BL et al. "Adenovirus vectors with the 100K gene deleted and their potential for multiple gene therapy applications." (2001) J Virol 75:5913-20.
Holbro, T et al. "The ErbB2/ErbB3 heterodimer functions as an oncogenic unti: ErbB2 requires ErbB3 to drive breast tumer cell proliferation." (2003) Proc Natl Acad Sci USA 100:8933-8.
Holmes, E.H., "PSMA specific antibodies and their diagnostic and therapeutic use," (2001) Exp. Opin. Invest. Drugs 10(3):511-519.
Hsieh AC, et al. Targeting HER proteins in cancer therapy and the role of the non-target HER3. Br J Cancer. 2007;97(4):453-7.
Huang, X et al. "Heterotrimerization of the growth factor receptors erbB2, erbB3, and insulin-like growth facotr-l receptor in breast cancer cells resistant to herception." (2010) Cancer Res 70:1204-14.
Ignatiadis, M. et al. "Luminal breast cancer: from biology to treatment" (2013) Nature Rev Clin Oncol 10, 494-506.
Junttila TT, et al. Ligand-independent HER2/HER3/PI3K complex is disrupted by trastuzumab and is effectively inhibited by the PI3K inhibitor GDC-0941. Cancer Cell. 2009; 15(5):429-40.
Karyampudi L, et al. Accumulation of memory precursor CD8 T cells in regressing tumors following combination therapy with vaccine and anti-PD-1 antibody. Cancer Res. 2014;74(11):2974-85.
Kennecke, H. et al., "Metastatic behavior of breast cancer subtypes" (2010) J Oncol 28(20): 3271-3277.
Kershaw, M.H. et al., "Gene-engineered T cells as a superior adjuvant therapy for metastatic cancer" (2004) J Immunol 173(3): 2143-2150.
Kol A, et al. HER3, serious partner in crime: therapeutic approaches and potential biomarkers for effect of HER3-targeting. Pharmacol Ther. 2014;143(1):1-11.

(56) References Cited

OTHER PUBLICATIONS

Kwong, K.Y. & Hung, M.C. "A novel splice variant of HER2 with increased transformation activity" (1998) Mol Carcinog 23(2):62-68.

Laheru, DA et al. "Genes to vaccines for immunotherapy: how the molecular biology revolution has influenced cancer immunology." (2005) Mol Cancer Ther 4:1645-52.

* cited by examiner

Fig. 5A In vivo growth of HER2d16 in MM3MG Cells (in SCID-beige mice)

SEQUENCE LISTING

<160> NUMBER OF SEQ ID NOS: 12

<210> SEQ ID NO 1
<211> LENGTH: 3720
<212> TYPE: DNA
<213> ORGANISM: Homo sapien

<400> SEQUENCE: 1

```
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac cagggctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag gcacccagct cttttgaggac aactatgccc tggccgtgct agacaatgga     360
gacccgctga caataccac ccctgtcaca ggggcctccc caggaggcct gcgggagctg     420
cagcttcgaa gcctcacaga gatcttgaaa ggaggggtct tgatccagcg gaaccccag      480 ctctgctacc aggacacgat tttgtggaag gacatcttcc acaagaacaa ccagctggct     540
ctcacactga tagacaccaa ccgctctcgg gcctgccacc cctgttctcc gatgtgtaag     600
ggctcccgct gctggggaga gagttctgag gattgtcaga gcctgacgcg cactgtctgt     660
gccggtggct gtgcccgctg caaggggcca ctgcccactg actgctgcca tgagcagtgt     720
gctgccggct gcacgggccc caagcactct gactgcctgg cctgcctcca cttcaaccac     780
agtggcatct gtgagctgca ctgcccagcc ctggtcacct acaacacaga cacgtttgag     840
tccatgccca atcccgaggg ccggtataca ttcggcgcca gctgtgtgac tgcctgtccc     900
tacaactacc tttctacgga cgtgggatcc tgcaccctcg tctgccccct gcacaaccaa     960
gaggtgacag cagaggatgg aacacagcgg tgtgagaagt gcagcaagcc ctgtgcccga    1020
gtgtgctatg gtctgggcat ggagcacttg cgagaggtga gggcagttac cagtgccaat    1080
atccaggagt ttgctggctg caagaagatc tttgggagcc tggcatttct gccggagagc    1140
tttgatgggg acccagcctc caacactgcc ccgctccagc cagagcagct ccaagtgttt    1200
gagactctgg aagagatcac aggttaccta tacatctcag catggccgga cagcctgcct    1260
gacctcagcg tcttccagaa cctgcaagta atccggggac gaattctgca caatggcgcc    1320
tactcgctga cccctgcaagg gctggcatc agctggctgg gctgcgctc actgagggaa    1380 ctgggcagtg gactggccct catccaccat aacacccacc tctgcttcgt gcacacggtg    1440
ccctgggacc agctctttcg gaacccgcac aagctctgc tccacactgc caaccggcca    1500
gaggacgagt gtgtgggcga gggcctggcc tgccaccagc tgtgcgcccg agggcactgc    1560
tggggtccag gcccacccca gtgtgtcaac tgcagccagt tccttcgggg ccaggagtgc    1620
```

-continued

```
gtggaggaat gccgagtact gcaggggctc cccagggagt atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc atcaactgc acccactccc ctctgacgtc catcgtctct   1920
gcggtggttg gcattctgct ggtcgtggtc ttggggtgg tctttgggat cctcatcaag   1980
cgacggcagc agaagatccg aagtacacg atgcggagac tgctgcagga acggagctg   2040 gtggagccgc tgacacctag cggagcgatg cccaaccagg cgcagatgcg gatcctgaaa   2100
gagacggagc tgaggaaggt gaaggtgctt ggatctggcg cttttggcac agtctacaag   2160
ggcatctgga tccctgatgg ggagaatgtg aaaattccag tggccatcaa agtgttgagg   2220
gaaaacacat cccccaaagc caacaaagaa atcttagacg aagcatacgt gatggctggt   2280
gtgggctccc catatgtctc ccgccttctg gggatctgcc tgacatccac ggtgcagctg   2340
gtgacacagc ttatgcccta tggctgcctc ttagaccatg tccgggaaaa ccgcggacgc   2400
ctgggctccc aggacctgct gaactggtgt atgcagattg ccaaggggat gagctacctg   2460
gaggatgtgc ggctcgtaca cagggacttg gccgctcgga acgtgctggt caagagtccc   2520
aaccatgtca aaattacaga cttcgggctg gctcggctgc tggacattga cgagacagag   2580
taccatgcag atgggggcaa ggtgcccatc aagtggatgg cgctggagtc cattctccgc   2640
cggcggttca cccaccagag tgatgtgtgg agttatggtg tgactgtgtg ggagctgatg   2700
acttttgggg ccaaacctta cgatgggatc ccagcccggg agatccctga cctgctggaa   2760 aaggggagc ggctgcccca gccccccatc tgcaccattg atgtctacat gatcatggtc   2820
aaatgttgga tgattgactc tgaatgtcgg ccaagattcc gggagttggt gtctgaattc   2880
tcccgcatgg ccagggaccc ccagcgcttt gtggtcatcc agaatgagga cttgggccca   2940
gccagtccct tggacagcac cttctaccgc tcactgctgg aggacgatga catgggggac   3000
ctggtggatg ctgaggagta tctggtaccc cagcagggct tcttctgtcc agaccctgcc   3060
ccgggcgctg ggggcatggt ccaccacagg caccgcagct catctaccag gagtggcggt   3120
ggggacctga cactagggct ggagccctct gaagaggagg cccccaggtc tccactggca   3180
ccctccgaag gggctggctc cgatgtattt gatggtgacc tgggaatggg ggcagccaag   3240
gggctgcaaa gcctccccac acatgacccc agccctctac agcggtacag tgaggacccc   3300
acagtacccc tgccctctga gactgatggc tacgttgccc cctgacctg cagccccag   3360 cctgaatatg tgaaccagcc agatgttcgg ccccagcccc cttcgccccg agagggccct   3420
ctgcctgctg cccgacctgc tggtgccact ctggaaaggg ccaagactct ctccccaggg   3480
aagaatgggg tcgtcaaaga cgtttttgcc tttgggggtg ccgtggagaa ccccgagtac   3540
ttgacacccc agggaggagc tgcccctcag ccccaccctc ctcctgcctt cagcccagcc   3600
ttcgacaacc tctattactg ggaccaggac ccaccagagc ggggggctcc acccagcacc   3660
ttcaaaggga cacctacggc agagaaccca gagtacctgg gtctggacgt gccagtgtga   3720
```

<210> SEQ ID NO 2
<211> LENGTH: 1239
<212> TYPE: PRT
<213> ORGANISM: Homo sapien

<400> SEQUENCE: 2

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400
```

```
Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Pro Leu Thr Ser Ile Val Ser
625                 630                 635                 640

Ala Val Val Gly Ile Leu Leu Val Val Val Leu Gly Val Val Phe Gly
                645                 650                 655

Ile Leu Ile Lys Arg Arg Gln Gln Lys Ile Arg Lys Tyr Thr Met Arg
            660                 665                 670

Arg Leu Leu Gln Glu Thr Glu Leu Val Glu Pro Leu Thr Pro Ser Gly
        675                 680                 685

Ala Met Pro Asn Gln Ala Gln Met Arg Ile Leu Lys Glu Thr Glu Leu
    690                 695                 700

Arg Lys Val Lys Val Leu Gly Ser Gly Ala Phe Gly Thr Val Tyr Lys
705                 710                 715                 720

Gly Ile Trp Ile Pro Asp Gly Glu Asn Val Lys Ile Pro Val Ala Ile
                725                 730                 735

Lys Val Leu Arg Glu Asn Thr Ser Pro Lys Ala Asn Lys Glu Ile Leu
            740                 745                 750

Asp Glu Ala Tyr Val Met Ala Gly Val Gly Ser Pro Tyr Val Ser Arg
        755                 760                 765

Leu Leu Gly Ile Cys Leu Thr Ser Thr Val Gln Leu Val Thr Gln Leu
    770                 775                 780

Met Pro Tyr Gly Cys Leu Leu Asp His Val Arg Glu Asn Arg Gly Arg
785                 790                 795                 800

Leu Gly Ser Gln Asp Leu Leu Asn Trp Cys Met Gln Ile Ala Lys Gly
                805                 810                 815
```

```
Met Ser Tyr Leu Glu Asp Val Arg Leu Val His Arg Asp Leu Ala Ala
                820                 825                 830

Arg Asn Val Leu Val Lys Ser Pro Asn His Val Lys Ile Thr Asp Phe
            835                 840                 845

Gly Leu Ala Arg Leu Leu Asp Ile Asp Glu Thr Glu Tyr His Ala Asp
            850                 855                 860

Gly Gly Lys Val Pro Ile Lys Trp Met Ala Leu Glu Ser Ile Leu Arg
865                 870                 875                 880

Arg Arg Phe Thr His Gln Ser Asp Val Trp Ser Tyr Gly Val Thr Val
                885                 890                 895

Trp Glu Leu Met Thr Phe Gly Ala Lys Pro Tyr Asp Gly Ile Pro Ala
            900                 905                 910

Arg Glu Ile Pro Asp Leu Leu Glu Lys Gly Glu Arg Leu Pro Gln Pro
            915                 920                 925

Pro Ile Cys Thr Ile Asp Val Tyr Met Ile Met Val Lys Cys Trp Met
            930                 935                 940

Ile Asp Ser Glu Cys Arg Pro Arg Phe Arg Glu Leu Val Ser Glu Phe
945                 950                 955                 960

Ser Arg Met Ala Arg Asp Pro Gln Arg Phe Val Val Ile Gln Asn Glu
                965                 970                 975

Asp Leu Gly Pro Ala Ser Pro Leu Asp Ser Thr Phe Tyr Arg Ser Leu
            980                 985                 990

Leu Glu Asp Asp Asp Met Gly Asp Leu Val Asp Ala Glu Glu Tyr Leu
            995                 1000                1005

Val Pro Gln Gln Gly Phe Phe Cys Pro Asp Pro Ala Pro Gly Ala
            1010                1015                1020

Gly Gly Met Val His His Arg His Arg Ser Ser Ser Thr Arg Ser
            1025                1030                1035

Gly Gly Gly Asp Leu Thr Leu Gly Leu Glu Pro Ser Glu Glu Glu
            1040                1045                1050

Ala Pro Arg Ser Pro Leu Ala Pro Ser Glu Gly Ala Gly Ser Asp
            1055                1060                1065

Val Phe Asp Gly Asp Leu Gly Met Gly Ala Ala Lys Gly Leu Gln
            1070                1075                1080

Ser Leu Pro Thr His Asp Pro Ser Pro Leu Gln Arg Tyr Ser Glu
            1085                1090                1095

Asp Pro Thr Val Pro Leu Pro Ser Glu Thr Asp Gly Tyr Val Ala
            1100                1105                1110

Pro Leu Thr Cys Ser Pro Gln Pro Glu Tyr Val Asn Gln Pro Asp
            1115                1120                1125

Val Arg Pro Gln Pro Pro Ser Pro Arg Glu Gly Pro Leu Pro Ala
            1130                1135                1140

Ala Arg Pro Ala Gly Ala Thr Leu Glu Arg Ala Lys Thr Leu Ser
            1145                1150                1155

Pro Gly Lys Asn Gly Val Val Lys Asp Val Phe Ala Phe Gly Gly
            1160                1165                1170

Ala Val Glu Asn Pro Glu Tyr Leu Thr Pro Gln Gly Gly Ala Ala
            1175                1180                1185

Pro Gln Pro His Pro Pro Ala Phe Ser Pro Ala Phe Asp Asn
            1190                1195                1200

Leu Tyr Tyr Trp Asp Gln Asp Pro Pro Glu Arg Gly Ala Pro Pro
            1205                1210                1215
```

Ser Thr Phe Lys Gly Thr Pro Thr Ala Glu Asn Pro Glu Tyr Leu
    1220              1225                1230

Gly Leu Asp Val Pro Val
    1235

<210> SEQ ID NO 3
<211> LENGTH: 335
<212> TYPE: DNA
<213> ORGANISM: Homo sapien

<400> SEQUENCE: 3

| | | | | | |
|---|---|---|---|---|---|
| atggagctgg | cggccttgtg | ccgctggggg | ctcctcctcg | ccctcttgcc | ccccggagcc | 60 |
| gcgagcaccc | aagtgtgcac | cggcacagac | atgaagctgc | ggctccctgc | cagtcccgag | 120 |
| acccacctgg | acatgctccg | ccacctctac | cagggctgcc | aggtggtgca | gggaaacctg | 180 |
| gaactcacct | acctgcccac | caatgccagc | ctgtccttcc | tgcaggatat | ccaggaggtg | 240 |
| cagggctacg | tgctcatcgc | tcacaaccaa | gtgaggcagg | tcccactgca | gaggctgcgg | 300 |
| attgtgcgag | gcacccagct | ctttgaggac | aacta | | | 335 |

<210> SEQ ID NO 4
<211> LENGTH: 111
<212> TYPE: PRT
<213> ORGANISM: Homo sapien

<400> SEQUENCE: 4

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn
            100                 105                 110

<210> SEQ ID NO 5
<211> LENGTH: 3720
<212> TYPE: DNA
<213> ORGANISM: Homo sapien

<400> SEQUENCE: 5

| | | | | | |
|---|---|---|---|---|---|
| atggagctgg | cggccttgtg | ccgctggggg | ctcctcctcg | ccctcttgcc | ccccggagcc | 60 |
| gcgagcaccc | aagtgtgcac | cggcacagac | atgaagctgc | ggctccctgc | cagtcccgag | 120 |
| acccacctgg | acatgctccg | ccacctctac | cagggctgcc | aggtggtgca | gggaaacctg | 180 |
| gaactcacct | acctgcccac | caatgccagc | ctgtccttcc | tgcaggatat | ccaggaggtg | 240 |
| cagggctacg | tgctcatcgc | tcacaaccaa | gtgaggcagg | tcccactgca | gaggctgcgg | 300 |
| attgtgcgag | gcacccagct | ctttgaggac | aactatgccc | tggccgtgct | agacaatgga | 360 |
| gacccgctga | acaataccac | ccctgtcaca | ggggcctccc | caggaggcct | gcgggagctg | 420 |
| cagcttcgaa | gcctcacaga | gatcttgaaa | ggaggggtct | tgatccagcg | gaaccccag | 480 |

```
ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgcccccct gcacaaccaa    960 gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccagggagt atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactccc ctctgacgtc catcgtctct   1920
gcggtggttg gcattctgct ggtcgtggtc ttggggtgg tctttgggat cctcatcaag   1980
cgacggcagc agaagatccg gaagtagacg atgcggagac tgctgcagga acggagctg   2040 gtggagccgc tgacacctag cggagcgatg cccaaccagg cgcagatgcg gatcctgaaa   2100
gagacggagc tgaggaaggt gaaggtgctt ggatctggcg cttttggcac agtctacaag   2160
ggcatctgga tccctgatgg ggagaatgtg aaaattccag tggccatcaa agtgttgagg   2220
gaaaacacat cccccaaagc caacaaagaa atcttagacg aagcatacgt gatggctggt   2280
gtgggctccc catatgtctc ccgccttctg gggatctgcc tgacatccac ggtgcagctg   2340
gtgacacagc ttatgcccta tggctgcctc ttagaccatg tccgggaaaa ccgcggacgc   2400
ctgggctccc aggacctgct gaactggtgt atgcagattg ccaagggat gagctacctg   2460 gaggatgtgc ggctcgtaca cagggacttg gccgctcgga acgtgctggt caagagtccc   2520
aaccatgtca aaattacaga cttcgggctg gctcggctgc tggacattga cgagacagag   2580
taccatgcag atgggggcaa ggtgcccatc aagtggatgg cgctggagtc cattctccgc   2640
cggcggttca cccaccagag tgatgtgtgg agttatggtg tgactgtgtg ggagctgatg   2700
acttttgggg ccaaacctta cgatgggatc ccagcccggg agatccctga cctgctggaa   2760
aagggggagc ggctgcccca gccccccatc tgcaccattg atgtctacat gatcatggtc   2820
```

-continued

```
aaatgttgga tgattgactc tgaatgtcgg ccaagattcc gggagttggt gtctgaattc    2880
tcccgcatgg ccagggaccc ccagcgcttt gtggtcatcc agaatgagga cttgggccca    2940
gccagtccct tggacagcac cttctaccgc tcactgctgg aggacgatga catgggggac    3000
ctggtggatg ctgaggagta tctggtaccc cagcagggct tcttctgtcc agaccctgcc    3060
ccgggcgctg ggggcatggt ccaccacagg caccgcagct catctaccag gagtggcggt    3120
ggggacctga cactagggct ggagccctct gaagaggagg cccccaggtc tccactggca    3180
ccctccgaag gggctggctc cgatgtattt gatggtgacc tgggaatggg ggcagccaag    3240
gggctgcaaa gcctccccac acatgacccc agccctctac agcggtacag tgaggacccc    3300
acagtacccc tgccctctga gactgatggc tacgttgccc ccctgacctg cagcccccag    3360
cctgaatatg tgaaccagcc agatgttcgg ccccagcccc cttcgcccg agagggccct     3420 ctgcctgctg cccgacctgc tggtgccact ctggaaaggg ccaagactct ctccccaggg    3480
aagaatgggg tcgtcaaaga cgttttttgcc tttgggggtg ccgtggagaa ccccgagtac   3540
ttgacacccc agggaggagc tgcccctcag ccccacccte ctcctgcctt cagcccagcc    3600
ttcgacaacc tctattactg ggaccaggac ccaccagagc gggggggctcc acccagcacc   3660 ttcaaaggga cacctacggc agagaaccca gagtacctgg gtctggacgt gccagtgtga   3720
```

<210> SEQ ID NO 6
<211> LENGTH: 668
<212> TYPE: PRT
<213> ORGANISM: Homo sapien

<400> SEQUENCE: 6

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

-continued

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Pro Leu Thr Ser Ile Val Ser
625                 630                 635                 640
```

```
Ala Val Val Gly Ile Leu Leu Val Val Leu Gly Val Val Phe Gly
                    645             650             655
Ile Leu Ile Lys Arg Arg Gln Gln Lys Ile Arg Lys
                660             665
```

<210> SEQ ID NO 7
<211> LENGTH: 331
<212> TYPE: PRT
<213> ORGANISM: Homo sapien

<400> SEQUENCE: 7

```
Met Arg Ala Asn Asp Ala Leu Gln Val Leu Gly Leu Leu Phe Ser Leu
1               5                   10                  15
Ala Arg Gly Ser Glu Val Gly Asn Ser Gln Ala Val Cys Pro Gly Thr
                20                  25                  30
Leu Asn Gly Leu Ser Val Thr Gly Asp Ala Glu Asn Gln Tyr Gln Thr
            35                  40                  45
Leu Tyr Lys Leu Tyr Glu Arg Cys Glu Val Val Met Gly Asn Leu Glu
        50                  55                  60
Ile Val Leu Thr Gly His Asn Ala Asp Leu Ser Phe Leu Gln Trp Ile
65                  70                  75                  80
Arg Glu Val Thr Gly Tyr Val Leu Val Ala Met Asn Glu Phe Ser Thr
                85                  90                  95
Leu Pro Leu Pro Asn Leu Arg Val Val Arg Gly Thr Gln Val Tyr Asp
            100                 105                 110
Gly Lys Phe Ala Ile Phe Val Met Leu Asn Tyr Asn Thr Asn Ser Ser
        115                 120                 125
His Ala Leu Arg Gln Leu Arg Leu Thr Gln Leu Thr Glu Ile Leu Ser
130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                165                 170                 175
Lys Asp Asn Gly Arg Ser Cys Pro Pro Cys His Glu Val Cys Lys Gly
            180                 185                 190
Arg Cys Trp Gly Pro Gly Ser Glu Asp Cys Gln Thr Leu Thr Lys Thr
        195                 200                 205
Ile Cys Ala Pro Gln Cys Asn Gly His Cys Phe Gly Pro Asn Pro Asn
    210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
    290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Phe
                325                 330
```

<210> SEQ ID NO 8

```
<211> LENGTH: 1342
<212> TYPE: PRT
<213> ORGANISM: Homo sapien

<400> SEQUENCE: 8

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
370                 375                 380
```

```
Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                    405                 410                 415

Thr Ile Gly Gly Arg Ser Leu Tyr Asn Arg Gly Phe Ser Leu Leu Ile
                420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
        450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
                500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
        530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
                580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
        610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
                660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
                740                 745                 750

Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
        770                 775                 780

Leu Val Thr Gln Tyr Leu Pro Leu Gly Ser Leu Leu Asp His Val Arg
785                 790                 795                 800
```

```
Gln His Arg Gly Ala Leu Gly Pro Gln Leu Leu Asn Trp Gly Val
                805                 810                 815

Gln Ile Ala Lys Gly Met Tyr Tyr Leu Glu His Gly Met Val His
                820                 825                 830

Arg Asn Leu Ala Ala Arg Asn Val Leu Leu Lys Ser Pro Gln Val
                835                 840                 845

Gln Val Ala Asp Phe Gly Val Ala Asp Leu Leu Pro Pro Asp Asp Lys
850                         855                 860

Gln Leu Leu Tyr Ser Glu Ala Lys Thr Pro Ile Lys Trp Met Ala Leu
865                     870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
                900                 905                 910

Ala Gly Leu Arg Leu Ala Glu Val Pro Asp Leu Leu Glu Lys Gly Glu
                915                 920                 925

Arg Leu Ala Gln Pro Gln Ile Cys Thr Ile Asp Val Tyr Met Val Met
                930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
                980                 985                 990

His Gly Leu Thr Asn Lys Lys Leu Glu Glu Val Glu Leu Glu Pro Glu
                995                 1000                1005

Leu Asp Leu Asp Leu Asp Leu Glu Ala Glu Glu Asp Asn Leu Ala
                1010                1015                1020

Thr Thr Thr Leu Gly Ser Ala Leu Ser Leu Pro Val Gly Thr Leu
                1025                1030                1035

Asn Arg Pro Arg Gly Ser Gln Ser Leu Leu Ser Pro Ser Ser Gly
                1040                1045                1050

Tyr Met Pro Met Asn Gln Gly Asn Leu Gly Gly Ser Cys Gln Glu
                1055                1060                1065

Ser Ala Val Ser Gly Ser Ser Glu Arg Cys Pro Arg Pro Val Ser
                1070                1075                1080

Leu His Pro Met Pro Arg Gly Cys Leu Ala Ser Glu Ser Ser Glu
                1085                1090                1095

Gly His Val Thr Gly Ser Glu Ala Glu Leu Gln Glu Lys Val Ser
                1100                1105                1110

Met Cys Arg Ser Arg Ser Arg Ser Arg Ser Pro Arg Pro Arg Gly
                1115                1120                1125

Asp Ser Ala Tyr His Ser Gln Arg His Ser Leu Leu Thr Pro Val
                1130                1135                1140

Thr Pro Leu Ser Pro Pro Gly Leu Glu Glu Glu Asp Val Asn Gly
                1145                1150                1155

Tyr Val Met Pro Asp Thr His Leu Lys Gly Thr Pro Ser Ser Arg
                1160                1165                1170

Glu Gly Thr Leu Ser Ser Val Gly Leu Ser Ser Val Leu Gly Thr
                1175                1180                1185

Glu Glu Glu Asp Glu Asp Glu Glu Tyr Glu Tyr Met Asn Arg Arg
                1190                1195                1200
```

-continued

```
Arg Arg His Ser Pro Pro His Pro Pro Arg Pro Ser Ser Leu Glu
    1205            1210                1215

Glu Leu Gly Tyr Glu Tyr Met Asp Val Gly Ser Asp Leu Ser Ala
    1220            1225                1230

Ser Leu Gly Ser Thr Gln Ser Cys Pro Leu His Pro Val Pro Ile
    1235            1240                1245

Met Pro Thr Ala Gly Thr Thr Pro Asp Glu Asp Tyr Glu Tyr Met
    1250            1255                1260

Asn Arg Gln Arg Asp Gly Gly Pro Gly Gly Asp Tyr Ala Ala
    1265            1270                1275

Met Gly Ala Cys Pro Ala Ser Glu Gln Gly Tyr Glu Glu Met Arg
    1280            1285                1290

Ala Phe Gln Gly Pro Gly His Gln Ala Pro His Val His Tyr Ala
    1295            1300                1305

Arg Leu Lys Thr Leu Arg Ser Leu Glu Ala Thr Asp Ser Ala Phe
    1310            1315                1320

Asp Asn Pro Asp Tyr Trp His Ser Arg Leu Phe Pro Lys Ala Asn
    1325            1330                1335

Ala Gln Arg Thr
    1340

<210> SEQ ID NO 9
<211> LENGTH: 595
<212> TYPE: PRT
<213> ORGANISM: Homo sapien

<400> SEQUENCE: 9

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205
```

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
            245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
            325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
            405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
            485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
            515                 520                 525

Lys Cys Lys Asn Val Val Pro Leu Asn Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
            565                 570                 575

His Ser Leu Gln Lys Tyr Tyr Ile Thr Gly Glu Ala Glu Gly Phe Pro
                580                 585                 590

Ala Thr Val
    595

<210> SEQ ID NO 10
<211> LENGTH: 595

<212> TYPE: PRT
<213> ORGANISM: Homo sapien

<400> SEQUENCE: 10

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400
```

```
Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Ser Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 11
<211> LENGTH: 595
<212> TYPE: PRT
<213> ORGANISM: Homo sapien

<400> SEQUENCE: 11

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160
```

```
Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Gly Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575
```

His Ser Leu Gln Lys Tyr Tyr Ile Thr Gly Glu Ala Glu Gly Phe Pro
            580                 585                 590

Ala Thr Val
        595

<210> SEQ ID NO 12
<211> LENGTH: 595
<212> TYPE: PRT
<213> ORGANISM: Homo sapien

<400> SEQUENCE: 12

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Arg Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

-continued

```
Glu Leu Val His Met Ile Asn Trp Ala Lys Arg Val Pro Gly Phe Val
        355                 360                 365
Asp Leu Thr Leu His Asp Gln Val His Leu Leu Glu Cys Ala Trp Leu
        370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
                420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
        450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
                500                 505                 510
His Ile Arg His Met Ser Asn Lys Gly Met Glu His Leu Tyr Ser Met
        515                 520                 525
Lys Cys Lys Asn Val Val Pro Leu Tyr Asp Leu Leu Leu Glu Met Leu
        530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
                580                 585                 590
Ala Thr Val
        595
```

VACCINES AGAINST AN ONCOGENIC ISOFORM OF HER2 (ErbB2) AND METHODS OF USING THE SAME

CROSS-REFERENCE TO RELATED APPLICATIONS

This patent application is a continuation of U.S. patent application Ser. No. 16/045,248, filed Jul. 25, 2018, and issuing as U.S. Pat. No. 10,842,857 on Nov. 24, 2020, which is a divisional of U.S. patent application Ser. No. 15/324,215, now abandoned, filed Jan. 5, 2017, which is a national stage filing under 35 U.S.C. § 371 of International Application No. PCT/US2015/039359, filed Jul. 7, 2015, which claims the benefit of priority of U.S. Provisional Patent Application No. 62/021,554, filed Jul. 7, 2014, all of which are incorporated herein by reference in their entireties.

STATEMENT REGARDING FEDERALLY SPONSORED RESEARCH

This invention was made with United States government support awarded by the Department of Defense grant number BC113107. The United States has certain rights in this invention.

SEQUENCE LISTING

A Sequence Listing accompanies this application and is incorporated herein by reference in its entirety. The Sequence Listing was filed with the application as a text file on Jul. 7, 2015.

INTRODUCTION

This application relates to a cancer vaccine against HER2, specifically a vaccine against HER2 isoform antigens that are expressed on cancer cells or in response to development of resistance to a therapeutic intervention to cancer (or pre-cancers). Methods of using the vaccines and combination treatments including the vaccines in combination with immunomodulatory agents are also provided.

Cancer vaccines target antigens expressed by tumors, but application of these vaccines has not been as effective as once hoped due to induction of immune tolerance by chronic overexpression of the targeted protein in the absence of co-stimulatory molecules and the induction of an immunomodulatory environment. Preventative cancer vaccines may be more promising, but cancers are highly variable, with multiple genetic changes, but few truly universal changes. Thus, it is difficult to predict what antigens will be overexpressed on any specific cancer or whether an individual should be vaccinated and if so, with what antigens. In contrast, a strategy is proposed here in which vaccination against the antigen(s) that will predictably be overexpressed in response to a therapy, but prior to that antigen's overexpression by the cancer cells is used to induce a robust anti-cancer immune response.

SUMMARY

Provided herein is a mechanism of revolutionizing cancer therapy or prevention by preventing the development of resistance to cancer therapeutic or cancer prevention agents by identifying which antigens are likely to be expressed in a cancer or precancer in response to treatment with a cancer therapeutic or prevention agent and thus which antigens may be targeted with a vaccine in patients.

A vaccine targeting a specific antigen involved in a resistance mechanism, namely HER2d16, and methods of using the vaccine are provided. In one aspect, the vaccine includes a polynucleotide encoding a HER2 polypeptide. For example, a HER2 polypeptide of SEQ ID NO: 2, SEQ ID NO: 4, SEQ ID NO: 6 or portions thereof may be included in a vaccine.

In another aspect, methods of treating a cancer or precancer or reducing the likelihood of the cancer or precancer to develop resistance to a cancer therapeutic or cancer prevention agent by administering the vaccine provided herein to a subject with cancer or precancer are provided. The vaccine may be administered before, concurrently with or after administration of the cancer therapeutic or prevention agent or a checkpoint inhibitor immunomodulatory agent.

BRIEF DESCRIPTION OF THE DRAWINGS

FIG. 5A-5C are a set of data showing the in vivo growth effects of HER2d16 expression in tumors. FIG. 5A shows that the HER2d16 expressing cells grew more rapidly than untransformed or HER2 expressing cells. The table of FIG. 5B shows that only the HER2d16 expressing cells were able to kill any of the mice and that HER2d16 is highly transformative in murine mammary cells in vivo. FIG. 5C is a photograph comparing the tumors from HER2 expressing and HER2d16 expressing tumors. MM3MG cells stably expressing the indicated genes were implanted subcutaneously into SCID-Beige mice (100,000 per mouse in PBS) at day 0. Tumor growth was measured by calipers at the indicated days (N=5, bars represent SE).

DETAILED DESCRIPTION

Figure 1B:
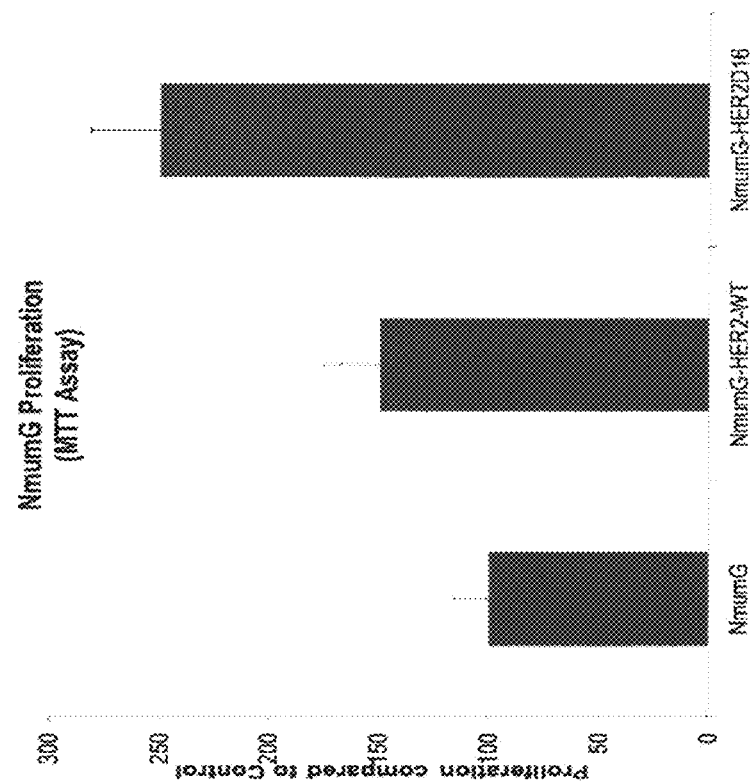
FIG. 1A-1B are a set of graphs showing that expression of HER2d16 in murine mammary cells can but does not always confer a proliferative advantage on the cells. MM3MG (FIG. 1A) and NMuMG (FIG. 1B) cells stably expressing the indicated genes were plated in 96-well plates (5,000 per well) and assessed at 4 days post-plating by MTT Assay (N=6, bars indicate SD).

As a novel alternative to vaccines targeting well established tumor antigens, we hypothesized that the antigen-specific immune non-responsiveness to conventional tumor-associated antigens may be avoided by targeting tumor antigens that are induced after exposure to a cancer therapeutic or prevention agent as a mechanism of developing therapeutic resistance. Although there may be many potential antigens overexpressed in response to a cancer therapeutic or prevention agent, those antigens that are likely critical components of specific therapeutic resistance mechanisms would be attractive targets, as immunologic ablation of clones expressing such antigens should eliminate the clinical recurrence of therapy resistant tumor cells. One such antigen thought to be essential to therapeutic resistance is a member of the HER family of receptor tyrosine kinases (RTKs), and to endocrine therapies, HER2.

HER2 is a preferred dimerization partner for other HER proteins with which it heterodimerizes. Dimerization with HER2 results in the autophosphorylation of tyrosine residues within the cytoplasmic domain of the receptors and initiates a variety of signaling pathways. HER2 has tumor promoting functions in some cancers, and amplification or over-expression of HER2 is associated with increased disease recurrence and poor prognosis. Treatment of HER2-amplified breast cancers with HER2-targeting tyrosine kinase inhibitors (TKIs) leads to an increase in HER3 expression and downstream signaling that results in therapeutic resistance.

For example, the anti-HER2 monoclonal antibody pertuzumab disrupts neuregulin-induced HER2-HER3 dimerization and signaling; however, it is less effective at disrupting the elevated basal state of ligand-independent HER2-HER3 interaction and signaling in HER2-overexpressing tumor cells. Other HER3-specific antibodies under development bind to, and cause internalization of, HER3, inhibiting downstream signaling. As an alternative to monoclonal antibodies, we have recently demonstrated that polyclonal antibodies induced by vaccination against receptors such as HER2 and HER3 can mediate profound receptor internalization and degradation, providing a therapeutic effect in vitro and in vivo (Ren et al., Breast cancer Research 2012 14: R89 and International Patent Application No. WO 2013/110030).

A vaccine composed of one or multiple forms of the HER2 gene deleted for exon 16 (48 bp deletion starting at nucleotide 1899 or portions thereof) encoded by a platform that would elicit an immune response to epitopes of this gene is provided herein. While we have targeted wild-type HER2 through vaccination, the approach described herein would selectively target a novel isoform that may be the critical driver for HER2-mediated tumorigenesis. We expect that more selectively targeting this specific oncogenic form of HER2 would allow for effective anti-cancer and HER2 signaling therapies mediated through immune targeting.

This invention would optimally be utilized through the inclusion of this gene referred to herein as HER2d16 (or HER2Δ16). The nucleic acid and amino acid sequence of HER2d16 is provided in SEQ ID NO: 1 and 2, respectively. Alternatively additional forms of this gene which are truncated or inactivated or peptide/epitopes of this gene in different immune stimulatory vector systems are also provided. One HER2d16 inactivated form is shown as HER2d16Ki and the nucleic acid and amino acid sequences are provided as SEQ ID NO: 3 and SEQ ID NO: 4, respectively. One truncation of HER2D16, called HER2d16TM and the nucleic acid and amino acid sequences are provided as SEQ ID NO: 5 and SEQ ID NO: 6, respectively. The portion of HER2d16 included in the vaccine should include the junction of the deletion in exon 16 in various isoforms. The deletion of exon 16 begins at amino acid 633 in the amino acid sequence of SEQ ID NO: 2. The B and T cell epitopes being recognized after vaccination in the examples have not been identified, but those of skill in the art would expect the epitopes to be 6, 8, 10, 12, 14, 16, 18 or 20 amino acids in length. The vaccines used in the Examples encompass larger polypeptides (at least 110 amino acids long), but vaccines may include smaller portions of the HER2d16 polypeptides than those provided herein. Suitably the vaccines include the region flanking the deletion at amino acid 633 of SEQ ID NO: 2 and include at least 8, 10, 12, 14, 16, 18, 20 or more amino acids.

The polynucleotide encoding the HER2d16 may be encompassed in a vaccine vector. For example, SEQ ID NO: 2, 4, 6 or portions thereof may be comprised in a vaccine. Suitable vaccine vectors include, but are not limited to viral vectors such as adenoviral, fowlpox, vaccinia, VEE, etc., DNA-based vaccination vectors, or protein/peptide vaccination strategies. Liposomes or bacterial vaccine vectors may also be suitable. This immunotherapeutic platform could be used prior to the development of cancer types dependent upon HER2-mediated signaling, used in front line or adjuvant settings as a treatment for these cancers, and also as a preventive measure to prohibit the development and evolution of this signaling pathway as a resistance pathway.

The vaccines or vaccine vectors may include polynucleotides encoding additional polypeptides, such as HER3, ESR1 or polypeptides of either of these comprising mutations such as those provided in SEQ ID NOs: 7-12, or any of the epitopes provided in International Publication No. WO2013/110030, which is incorporated herein by reference in its entirety. The vaccines or vaccine vectors may also include or be administered in conjunction with a checkpoint inhibitory immunomodulatory agent. The checkpoint inhibitory immunomodulatory agent may be an antibody antagonistic for CTLA-4 or PD1. In the Examples a PD1 antibody obtained from BioXCell called RMP1-14 and a CTLA-4 antibody from BioXCell called 9D9 were used. Other similar antibodies are commercially available or in clinical trials such as ipilimumab and nivolumab.

This would be easily distinguished from our and other prior approaches targeting HER2 as the deletion of a portion of this gene renders this as a novel isoform of HER2 with enhanced oncogenic potential. As such, vaccines targeting this isoform will elicit a different epitope repertoire for immune targeting and potentially a more significant anti-tumor effect. The HER2d16 mutant is associated with resistance to cancer therapeutics and thus targeting the specific isoform may result in a reduction of escape mutants or may block any escape mutants cancer cells from proliferating and thus block or reduce the development of resistance to the therapeutic agent.

Generation of resistance to cancer therapeutic or prevention agents is a common problem in the treatment of cancer or precancer and in several cases the mechanism of resistance to the therapeutic agent is known. Resistance is often the result of changes in gene expression (over-expression or blocked expression of a protein), change in the gene by mutation, or altered sequences by altered splicing or translocation or altered activation of a protein in the cells (over-activation or blocked activation of a protein).

In those cases where over-expression or over-activation of a protein, or a new sequence in the protein is responsible for increasing the resistance of the cancer or precancer cells to the therapeutic or prevention agent, we report a method for reducing the likelihood that the cancer or precancer will develop resistance to the cancer therapeutic or prevention agent. As used herein, resistance to a cancer therapeutic or prevention agent indicates that the cancer therapeutic or prevention agent is not as effective at inhibiting the growth of, or killing, cancer or precancer cells in response to the cancer therapeutic or prevention agent. The method may even block the development of resistance to the cancer therapeutic or prevention agent or may reverse resistance to the cancer therapeutic or prevention agent after it has developed. The methods include administering the cancer therapeutic or prevention agent and administering a vaccine to the subject in need of treatment for a cancer. The vaccine comprises a polynucleotide encoding a polypeptide whose expression or activation is correlated with or results in development of resistance of the cancer or precancer to the cancer therapeutic or prevention agent. The vaccines provided herein include a HER2 polypeptide or a polynucleotide encoding a HER2 polypeptide such as the HER2d16 polypeptide.

The vaccine may be administered before, during or after treatment with a cancer therapeutic or prevention agent or may be administered simultaneously with the cancer therapeutic or prevention agent. The administration of the vaccine and the cancer therapeutic or prevention agent to the subject reduces the likelihood that the subject's cancer or precancer will develop resistance to the therapeutic or prevention agent as compared to a control subject with a similar cancer or precancer not administered the vaccine or as compared to the general likelihood of a population of subjects having the cancer or precancer. In some embodiments, the cancer or precancer in individuals administered both the vaccine and the therapeutic or prevention agent does not develop resistance to the cancer therapeutic or prevention agent and is treated. Alternatively, the growth of the cancer or precancer may be inhibited or the growth rate reduced. The administration of the vaccine and cancer therapeutic or prevention agent may also reverse resistance to the cancer therapeutic or prevention agent if the cancer or precancer is already resistant to the cancer therapeutic or prevention agent. In some embodiments, administration of the vaccine is sufficient to treat the cancer or inhibit the growth or kill the cancer. In other embodiments, the vaccine must be administered in conjunction with the cancer therapeutic or prevention agent or prior to development of resistance to the cancer therapeutic or prevention agent by the cancer.

The vaccine may include a polynucleotide encoding a HER2 polypeptide. The HER2d16 protein sequence is provided in SEQ ID NO: 2. The vaccine may comprise full-length HER2d16 or portions thereof such as shown in SEQ ID NO: 4 and SEQ ID NO: 6. For example, the vaccine may comprise only the extracellular domain or the extracellular domain plus the transmembrane domain or other portions of the HER2 polypeptide. Suitably the vaccine is capable of eliciting an immune response to HER2 in a subject administered the vaccine. The immune response may be a B cell or T cell response. Suitably the immune response includes an antibody response directed to HER2. The immune response may be directed to an epitope flanking or overlapping the deletion of exon 16. The immune response may be a polyclonal antibody response in which multiple epitopes of HER2 are recognized by antibodies.

HER2d16 contains a deletion in exon 16 of HER2. The deletion results in a unique junction section in the peptide and epitopes spanning this junction can be generated using the vaccines described herein. Those of skill in the art will appreciate that a vaccine including polynucleotides encoding only portions of full-length HER2, i.e. antigenic epitopes, may be used in the vaccines described herein. Portions of the HER2 including the junction site at the point of deletion can be included in the vaccine.

The vaccine may include a vaccine vector. The vaccine vector may be a bacterial, yeast, viral or liposomal vaccine vector. The vaccine may be a DNA vaccine as well and not include a vaccine vector. The vaccine vector may be an adenovirus, adeno-associated virus, fowlpox, vaccinia, viral equine encephalitis virus, venezuelan equine encephalitis virus or other viral vaccine vectors. One method for generating adenovirus vectors is provided in Luo et al., Nature Protocols, (2007) 2: 1236-1247, which is incorporated herein by reference. The vaccine vector may contain the HER2 polynucleotide or portions thereof. The vaccine vector may contain the HER2 polypeptide or portions thereof. The vaccine vector may express the HER2 polypeptide or portions thereof. HER2 polypeptide or portions thereof may be expressed on the surface or interior of the vaccine vector. HER2 polynucleotide or portions thereof may be carried within the vaccine vector and the HER2 polypeptide or portions thereof may be expressed only after vaccination. HER2 polypeptides or portions thereof may be expressed as a fusion protein or in conjunction with adjuvants or other immunostimulatory molecules to further enhance the immune response to the polypeptide.

Methods of treating a cancer or precancer, or of reducing the likelihood of the cancer or precancer developing resistance to a cancer therapeutic or prevention agent, are also provided. The methods include administering the vaccine as described above to a subject having cancer or precancer. The subject may be any mammal, suitably a human, domesticated animal such as a dog or cat, or a mouse or rat. A cancer therapeutic or prevention agent may be administered concurrently with, before or after administration of the vaccine.

The cancer therapeutic or prevention agents may be any agent capable of treating the cancer or inhibiting growth of cancer cells. Suitable agents include those which target HER2, HER1/EGFR, HER3, estrogen receptor or IGF1R. The therapeutic agent may be trastuzumab, lapatinib, pertuzumab or another HER2 targeting therapeutic agent or it may be an EGFR targeting therapeutic agent such as cetuximab or erlotanib, or it may be an anti-estrogen, or an agent that prevents estrogen synthesis such as an aromatase inhibitor. We have previously demonstrated that a HER3 vaccine can treat a HER2 positive cancer when used in combination with a therapeutic agent targeting HER2. A HER2d16 vaccine should work similarly and the deletion junction provides a unique site for vaccination to differentiate cancer or precancer cells from normal cells. Cancer cells often develop resistance to HER2 targeting therapeutic agents. Addition of vaccination with a HER2 vaccine or passively transferred polyclonal antibodies specific for HER2 resulted in blocking resistance, inhibited cancer cell growth and resulted in treatment of the cancer.

Suitably the vaccinated subject develops an immune response to HER2d16 in response to administration of the vaccine. The immune response may be an antibody or T cell immune response. For example the immune response may include antibody-dependent cellular cytotoxicity, polyclonal antibody response, complement dependent cellular cytotoxicity, cellular cytotoxicity, disruption of ligand binding, disruption of dimerization, mimicking ligand binding causing internalization of HER2, or degradation of HER2. The immune response may comprise an antibody response directed to at least a portion of HER2, suitably a portion including the junction of the deletion in exon 16. The immune response may be specific for a T cell or B cell epitope flanking or encompassing the deletion of exon 16 at amino acid 633 of SEQ ID NO: 2 or regions flanking the deletion of exon 16 in HER2d16.

Reduction of the development of resistance can be measured in several ways. The resistance of the vaccinated subject may be compared to a similar subject that was not vaccinated as in the Examples. Alternatively, the reduction may be measured based on statistics generated regarding the likelihood of an individual being treated with the therapeutic agent to develop resistance versus that of individuals treated with the therapeutic agent and vaccinated with HER2. The reduction in the likelihood of resistance of the cancer may also be measured by measuring the level of HER2 expression on the surface of cancer cells. HER2 expression is reduced on cancer cells after effective administration of the vaccine. The effectiveness of the vaccine in treating the cancer or reducing the likelihood of resistance can be measured by tracking the growth of the tumor or the growth rate of the tumor or cancer cells. A decrease in tumor size or in the rate of tumor growth is indicative of treatment of the cancer.

The cancer may be selected from any cancer capable of developing resistance to a therapeutic agent by increasing expression or activation of a protein by the cancer cells. In particular the cancer may be any cancer capable of developing resistance to a therapeutic agent which targets a HER family tyrosine kinase, suitably HER2, HER3, or EGFR or the estrogen receptor, suitably anti-estrogens. The cancer may develop resistance by increasing the expression of HER2 or deleting a portion of HER2 to avoid susceptibility to the therapeutic agent. Suitably the cancers are selected from breast, prostate, lung, ovarian, colon, rectal, pancreas, bladder, head and neck or liver cancers or precancers. The resistance may be due to a single or multiple changes, and the vaccine can target one or more of these changes, and/or include multiple antigens likely found in resistance cells, but not necessarily in all resistance cells.

Treating cancer includes, but is not limited to, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

Co-administration, or administration of more than one composition (i.e. a vaccine and a therapeutic agent or vaccine and a checkpoint inhibitory immunomodulatory agent) to a subject, indicates that the compositions may be administered in any order, at the same time or as part of a unitary composition. The two compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An effective amount or a therapeutically effective amount as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e. the vaccines and the therapeutic agents or checkpoint inhibitory agents) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal absorption. Thus the compositions may be formulated as an ingestable, injectable, topical or suppository formulation. The compositions may also be delivered with in a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce the growth of the cancer at least 10%, 20%, 30%, 40%, 50%, 60%, 70%, 80%, 90%, 100% or more as compared to no treatment or treatment with only the therapeutic agent. It is specifically contemplated that pharmaceutical preparations and compositions may palliate, block further growth or alleviate symptoms associated with the cancer without providing a cure, or, in some embodiments, may be used to cure the cancer and rid the subject of the disease.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The vaccine vector may be administered one time or more than one time to the subject to effectively boost the immune response against HER2. If the vaccine is provided as a vaccine vector, the vaccine vector may be administered based on the number of particles delivered to the subject (i.e. plaque forming units or colony forming units). The subject may be administered $10^{12}$, $10^{11}$, $10^{10}$, $10^9$, $10^8$, $10^7$ or $10^6$ particles.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Materials and Methods
Viral Vectors:
The HER2 delta 16 plasmid was generated by engineering of our LTR-2/erbB2 using a geneblock and Gibson Isothermal Assembly Mix (New England Biolabs, Ipswich, MA). Truncations and K753A mutations were performed using standard cloning techniques. These genes were cloned into adenoviral vectors, which were then generated as previously described[1]. The HER2 and HER2 16 genes were also cloned into lentiviral vectors (LX301 from Addgene and CDH from Systems Biosciences) and used to generated cell lines with stable expression of these genes. Dox Inducible expression lentiviral vectors were generated as previously described[2].
Cell Lines:
Breast epithelial cell lines MM3MG, NMuMG, and MCF-10AT were obtained from the American Tissue Culture Collection (ATCC), and were maintained according to ATCC recommendations. These lines were tested for *Mycoplasma* and DNA fingerprinted at the Duke Cell Culture Facility.
In Vitro Assays:
Proliferation of stable cells was determined by MTT assay using 5,000 cells/well over the course of 3 d (against control counterparts) in 96-well plates. MTT growth assessments were done using a Bio-Rad plate reader after cell solubilization in DMSO. Soft agar assays for stable cells were done as described[3]. Briefly, 50,000 cells/well were plated in 0.3% soft agar (on a base of 0.6% soft agar) and allowed to grow for a period of 2 wk in DMEM with 10% FBS. At the end of this time, colonies of >15 cells were counted and scored. In experiments using inducible expression systems, Dox was added to the media at a concentration of 2 µg/ml (replaced weekly). Wound Scratch Assays were performed using p1000 tips, washing wounded plates with PBS (2×) and applying media before staining with Crystal Violet at 16 hours post-wounding. Pictures were taken using an Olympus IX73 using a 10× magnification objective.

Figure 1A:
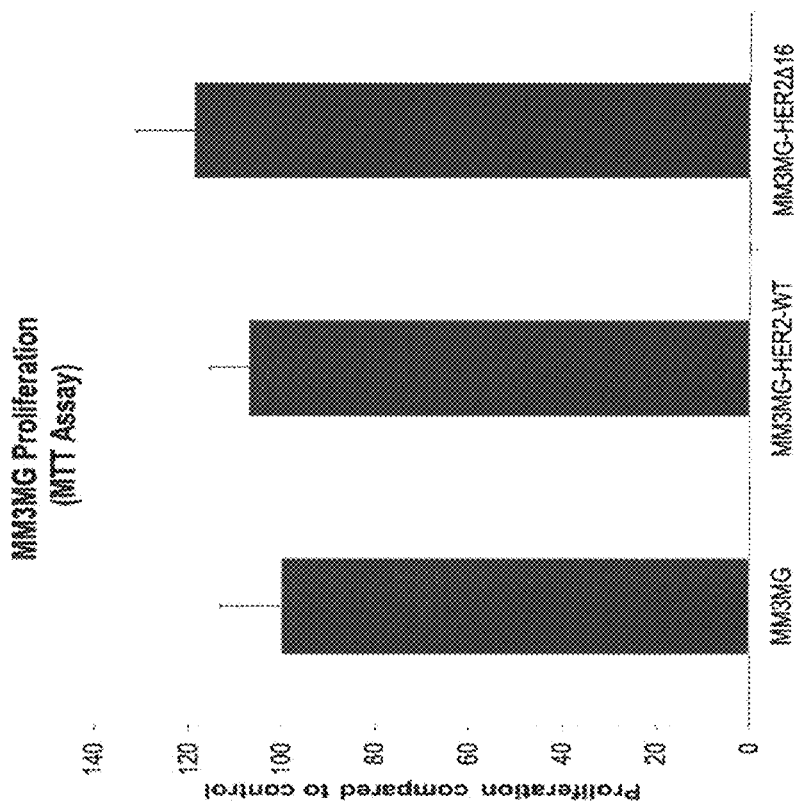
Figure 2B:
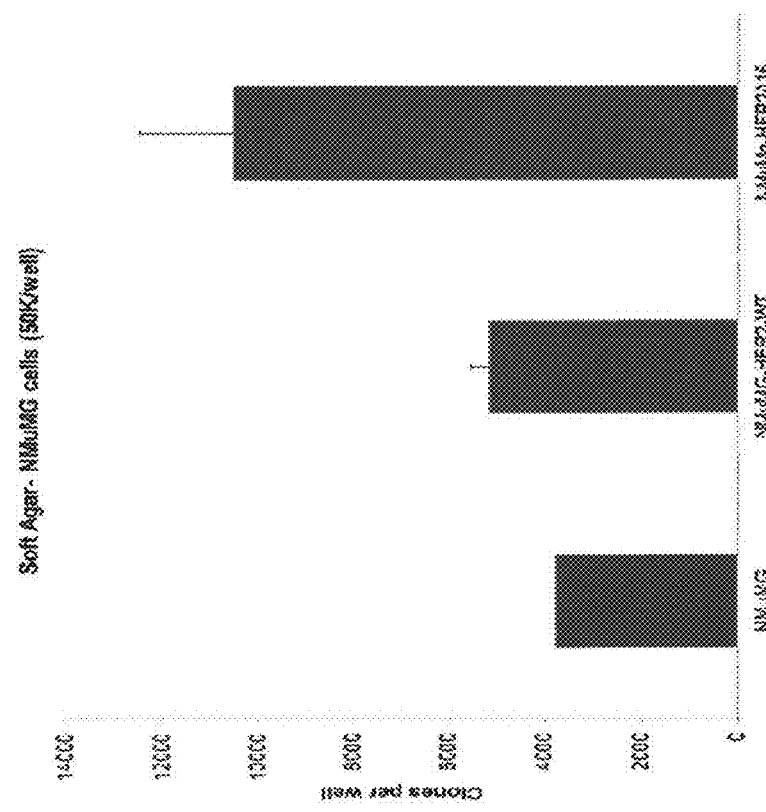
FIG. 2A-2B are a set of graphs showing that expression of HER2d16 in murine mammary cells does confer an advantage in anchorage-independent growth. MM3MG (FIG. 2A) and NMuMG (FIG. 2B) cells stably expressing the indicated genes were plated in 12-well dishes plates (50,000 per well) and assessed at 3 weeks days post-plating at 4× magnification (N=4, bars indicate SD) and the clones per well were counted.
Figure 2A:
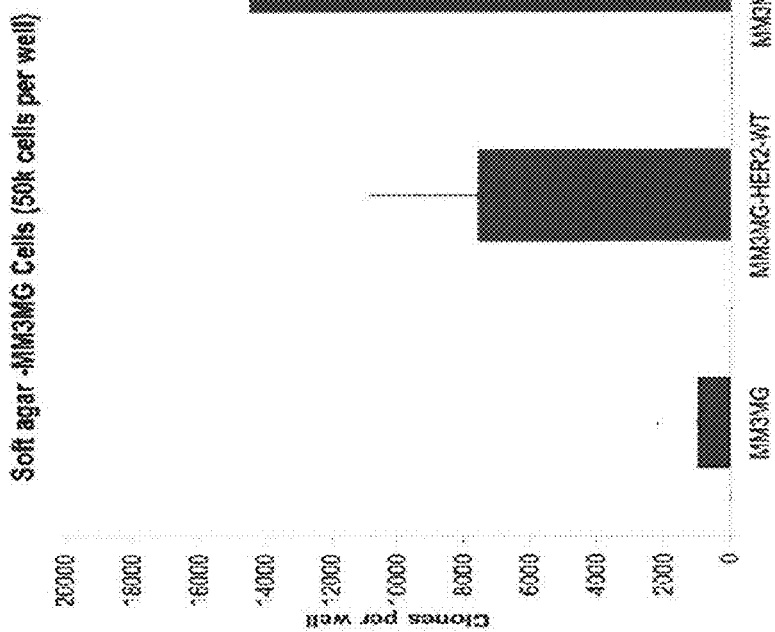
Figure 3:
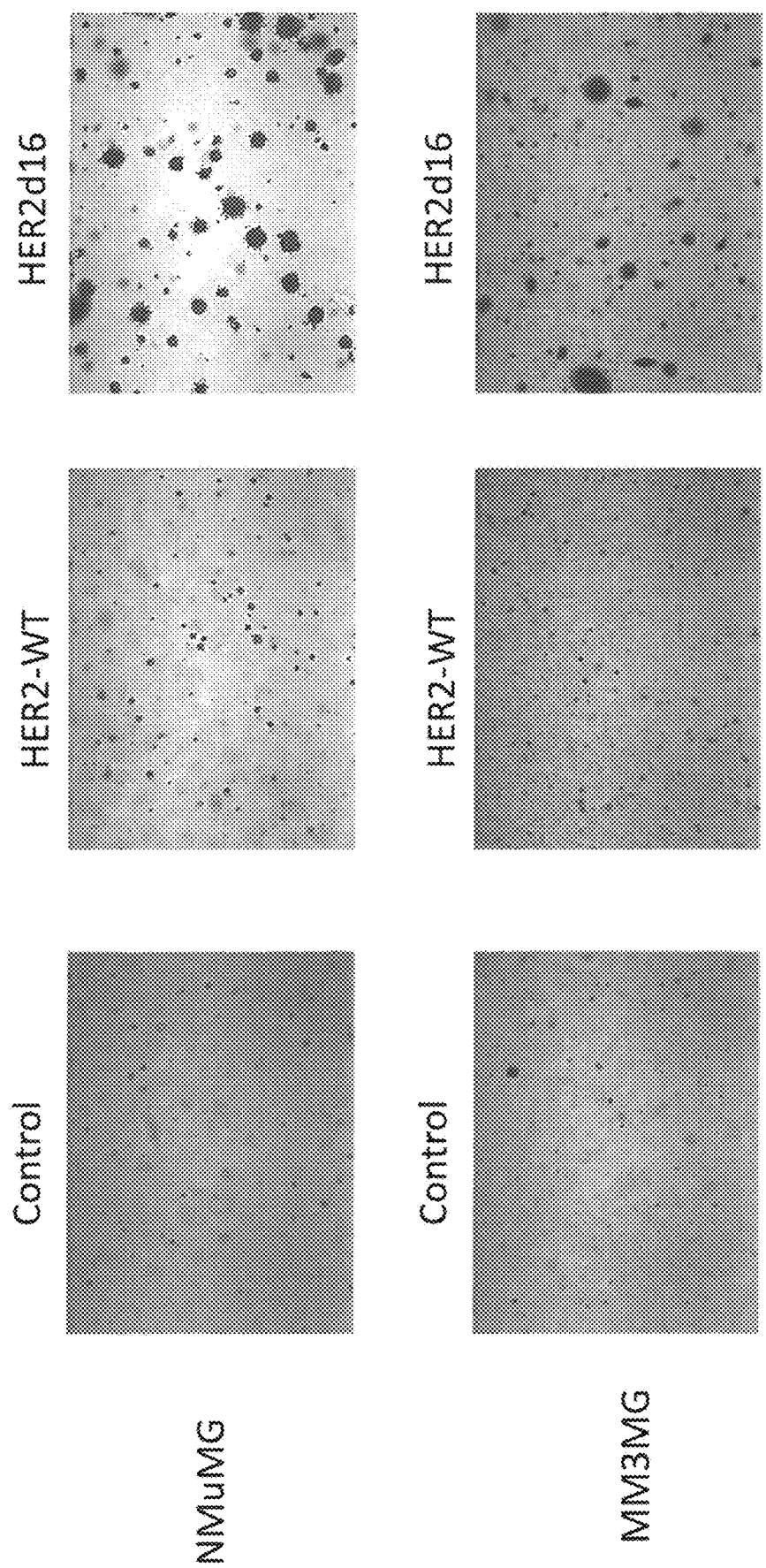
FIG. 3 is a set of photographs showing that HER2d16 expressed in murine mammary cells confers an advantage in anchorage-independent growth as compared to control cells or cells stably expressing HER2 wild-type. MM3MG and NMuMG cells stably expressing the indicated genes were plated in 12-well dishes plates (50,000 per well) and assessed at 3 weeks days post-plating at 4× magnification (N=4, bars indicate SD).

Animal Experiments:
Experiments using BALB/c, and SCID-Beige mice (obtained from Jackson Labs) were done in accordance with Duke Institutional Animal Care and Use Committee-approved protocols. For tumor vaccine experiments, Human HER2-transgenic mice (kindly provided by Dr. Wei-Zen Wei, Wayne State University, Detroit, MI[4]) were crossed with BALB/c mice (Jackson Labs) to permit implantation of MM3MG-HER2d16 tumors and genotyped by PCR as previously described[5]. In immnodeficient animals, stable cells were injected s.c. into the flank of SCID-beige mice (at indicated cells/animal) and measured as indicated. Tumor measurements were made using calipers and volumes calculated using the formula [v=width×width×(length/2)] whereas statistical differences were calculated using a mixed effects regression model using autoregressive covariance. In treatment experiments, T-DM1 was weekly delivered via tail vein (200 µg/mouse) while Lapatinib was given by oral gavage (5 times a week, 75 mg/kg). ELISPOT and ELISA Assays:
Immunogenicity experiments involved footpad injection of Ad-HER2d16-ki, Ad-HER2d16-ECD-TM, and Ad-GFP vectors (2.6×10$^{10}$ particles/mouse) in transgenic and naïve animals. Fourteen days postinjection, mice were euthanized and splenocytes and sera were collected for analysis. IFN-γ ELISPOT assays (Mabtech Inc.) were done according to the manufacturer's instructions using overlapping HER2 peptide mixes (2.6 µg/mL; BD Biosciences) as stimulating antigens and HIV-irrelevant overlapping peptide mixes as negative controls (BD Biosciences). Phorbol 12-myristate 13-acetate (50 ng/mL) and ionomycin (1 µg/mL) served as a positive control for splenocyte responsiveness. Antibodies were assessed using a cell-based ELISA method as previously described. Briefly, MCF-10AT and MCF-10AT-HER2d16 cells (engineered as with MM3MG cells) were plated overnight at 20,000 cells per well. The next day, serum was diluted and applied to the wells in quadruplicate and incubated at 4° C. for 2 hours. At this time point, cells were fixed for 10 minutes using a 10% Neutral Buffered Formalin Solution and then washed in PBS 5 times. After washing, an Anti-IgG-HRP secondary antibody was applied (Cell Signaling Technology, 1:1000 dilution) and incubated at 4° C. for an additional 1 hour. At this time point, cells were again washed five times with PBS and a TMB substrate solution applied for 10 minutes and read using a BioRad Plate Reader. Measurements from non-HER2d16 control cells were used to control for non HER2d16-specific binding.
Results:
In our previous research, we had demonstrated that HER2 can function as an oncogene in different cell-based systems, although this effect could be limited to certain cell types. To evaluate the impact of HER2d16 as an oncogenic driver of HER2+ breast cancer, we engineered HER2-WT and HER2d16 expression into two separate pre-malignant mouse mammary cells to ascertain and compare their relative impacts upon growth and transformation. Our experiments revealed that HER2d16 could affect enhanced proliferation in some cell lines (NMuMG) but not in other (MM3MG and MCF-10a) (FIGS. 1A-1B, and data not shown). Next, we employed a soft-agar assay to determine the impact of these genes on anchorage-independent growth of cells and determined that HER2d16 had a much more significant impact on anchorage-independent growth in comparison to HER2-WT (FIGS. 2A, 2B and 3). To confirm that this effect was independent of the integration site, we also employed a Dox-inducible system in NMuMG cells and again found that this effect was completely dependent upon HER2d16 expression (data not shown).

Figure 4:
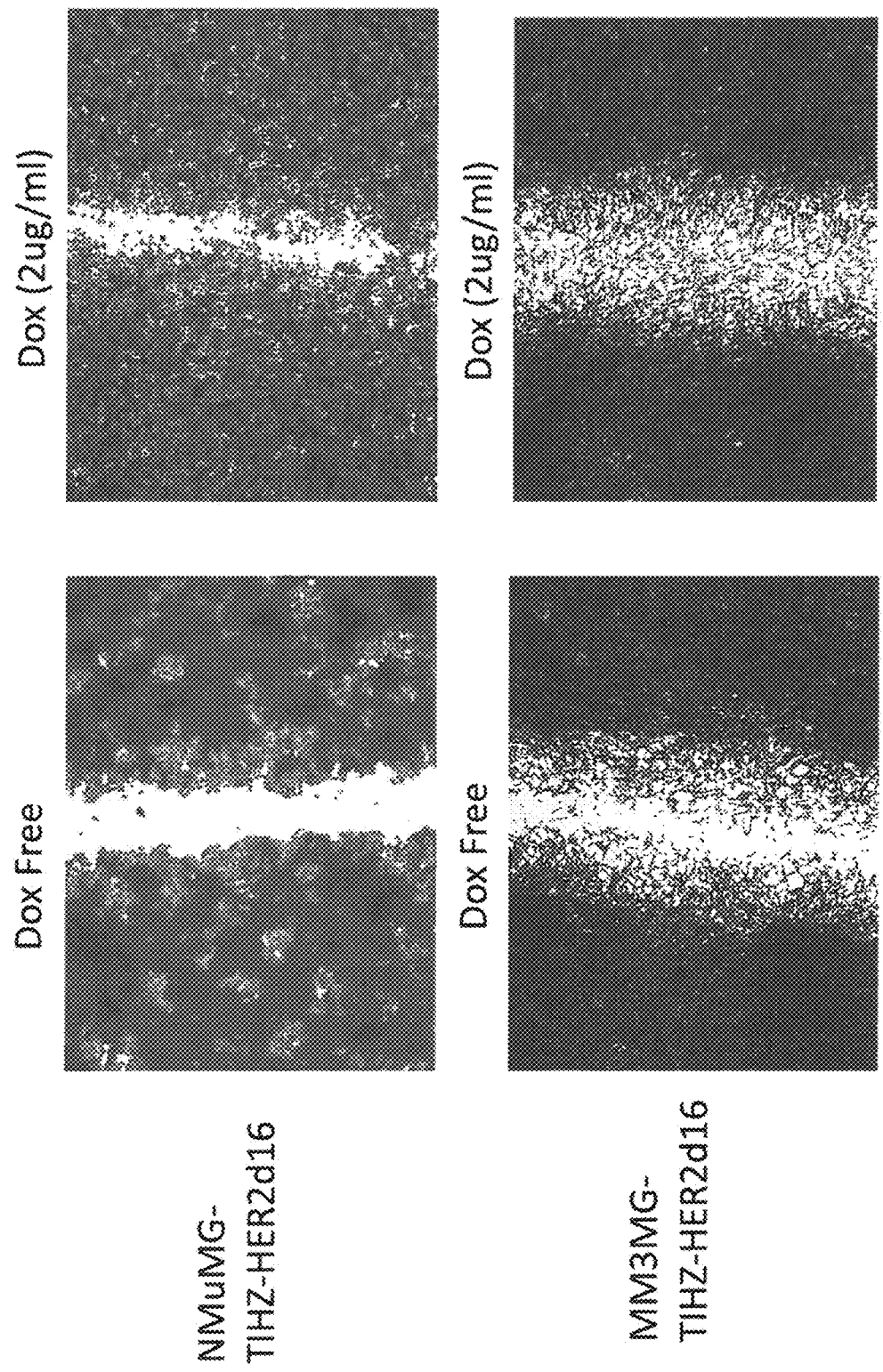
FIG. 4 is a set of photographs showing that HER2d16 stably expressed in murine mammary cells confers a significant enhanced migratory phenotype. MM3MG and NMuMG cells stably expressing the indicated genes were plated in 12-well dishes plates (250,000 per well). Wound Scratch Assays were performed using p1000 tips, washing wounded plates with PBS (2×) and applying media before staining with Crystal Violet at 16 hours post-wounding. Pictures were taken using an Olympus IX73 using a 10× magnification objective.

Having demonstrated a potent impact on Anchorage-independent growth, we also wished to see if this gene impacted other HER2-mediated behavior, such as cellular migration. HER2 has been demonstrated to impact cellular migration, so we employed a wound scratch assay using our inducible HER2d16 to explore the impact of HER2d16 expression on migration. Our results demonstrated a potent impact on cellular migration, in contrast to the minor impact demonstrated by HER2 expression (FIG. 4 and data not shown). While our results demonstrated that HER2d16 was more potent at impacting cellular behavior in comparison to HER2-WT in vitro, we next wanted to determine their relative impacts on oncogenicity in vivo.

Figure 5B:
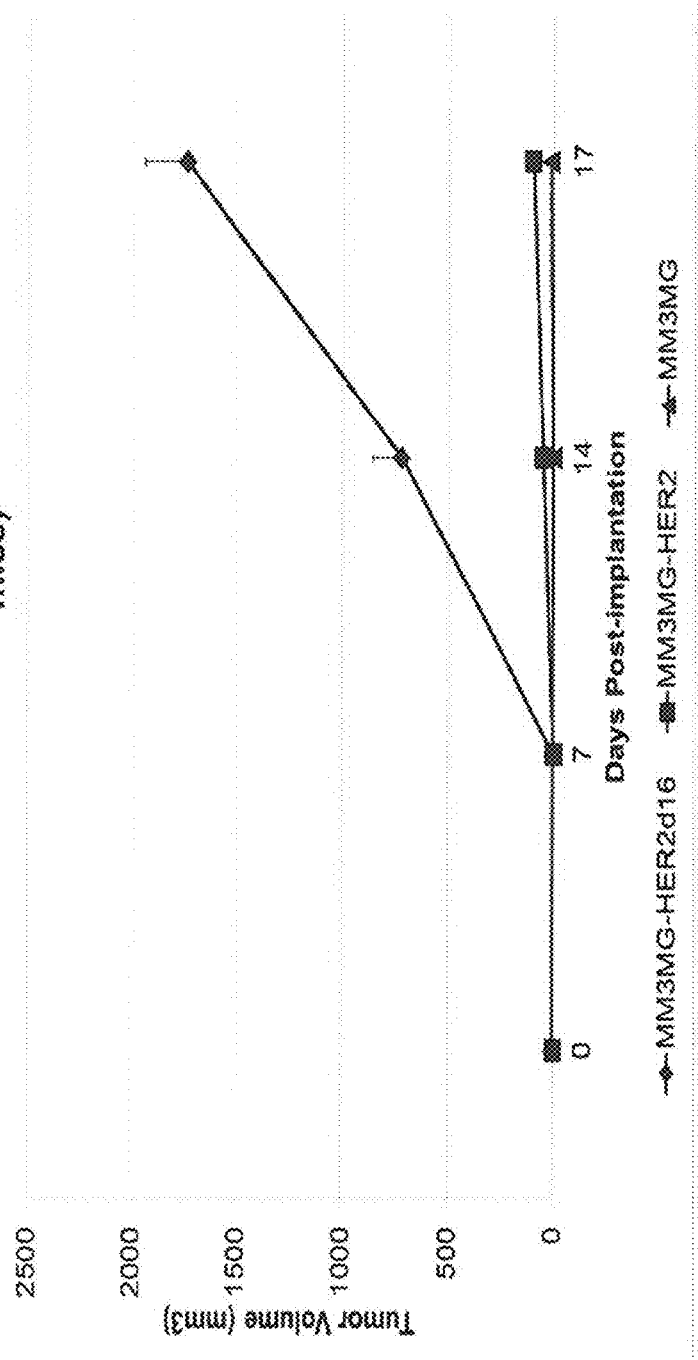
Figure 5C:
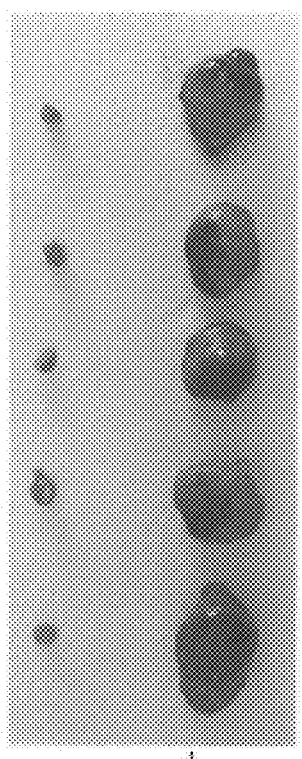

To confirm the impact of this isoform in vivo, we implanted MM3MG-HER2-WT and MM3MG-HER2d16 cell in mice and monitored tumor growth. While both HER2d16 and HER-WT cells formed tumors, we found that HER2d16 grew much more rapidly and formed much larger and more vascularized tumors in comparison to HER2-WT tumors in SCID-beige mice (FIG. 5A-5C). We also found that HER2-WT tumors would not form tumors in immuno-competent HER2 transgenic animals, but that HER2d16 would form tumors in the majority of these mice (FIG. 5A-5C). Thus, these results demonstrate that HER2d16 provide a potent oncogenic stimulus that is sufficient to circumvent anti-tumor immune responses in these syngeneic model systems.

Figure 6:
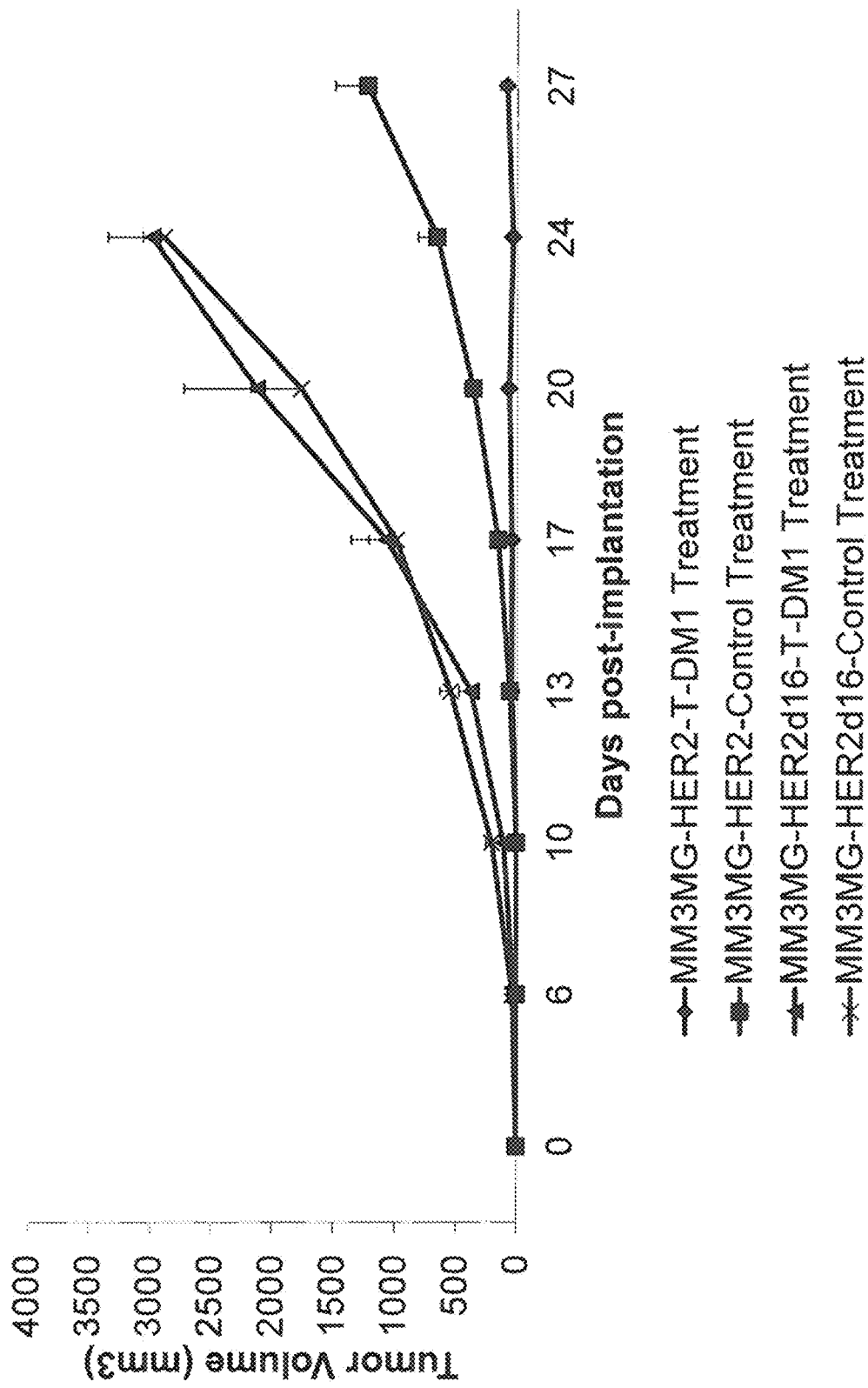
FIG. 6 is a graph showing that HER2d16 expressing murine mammary cells are more resistant to T-DM1 treatment than HER2-WT cells. MM3MG cells stably expressing the indicated genes were implanted subcutaneously into SCID-Beige mice (100,000 per mouse in PBS) at days 0. Mice were treated weekly with T-DM1 via tail vein injection (200 μg/mouse) beginning at day 10. Tumor growth was measured by calipers at the indicated days (N=5, bars represent SE).
Figure 7:
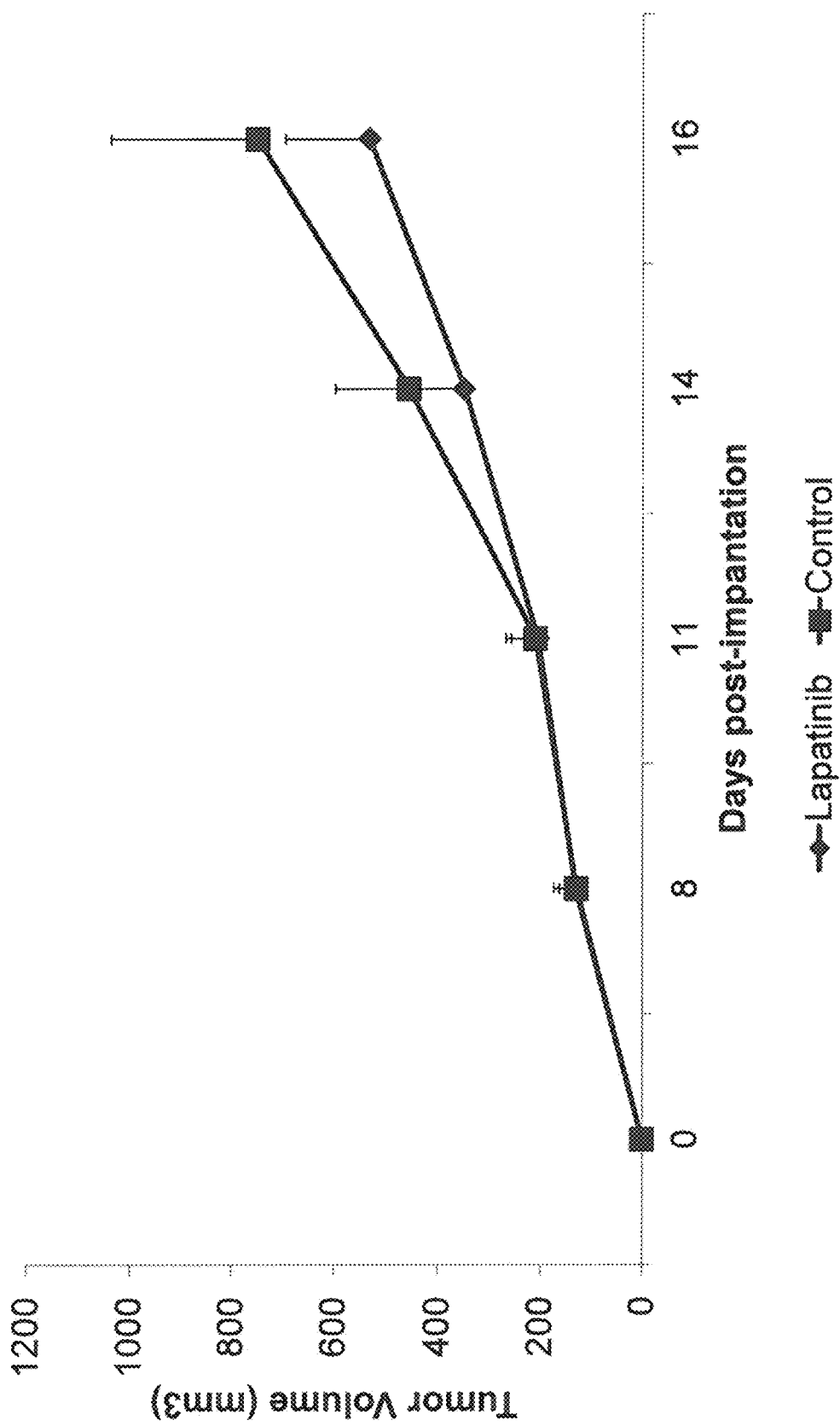
FIG. 7 is a graph showing that HER2d16 expressing murine mammary cells are resistant to lapatinib treatment in vivo. MM3MG cells stably expressing the indicated genes were implanted subcutaneously into SCID-Beige mice (100,000 per mouse in PBS) at days 0. Mice were treated weekly with lapatinib by oral gavage (75 mg/kg/5 days week) at day 8. Tumor growth was measured by calipers at the indicated days (N=5, bars represent SE).

While our previous results demonstrated that HER2d16 is a more potent oncogenic isoform in comparison to HER2, it was unknown if this isoform was resistant or sensitive to standard anti-HER2 therapies. Several papers have reported that HER2d16 is resistant to HER2-targeted therapies, while others have demonstrated that it is not[6-9]. As such, it was unclear to us if these discrepancies reflected differences between in vitro and in vivo assays, or if they were dependent upon the use of different models systems or experimental variables. To ascertain the impact in a more clinically relevant context, we chose to test the effect of Trastuzumab-DM1 (Kadcyla) and Lapatinib in our MM3MG in vivo model system. T-DM1 is the most efficacious clinical treatment for HER2+ breast cancer, combining the efficacy of Trastuzumab targeted monoclonals with an emnatsine therapeutic payload. Likewise, Lapatinib is a small molecule inhibitor of HER2 that represents a different type of targeted clinical agent, working through a different mechanism. Using these agents, we would determine if monoclonal therapies or small molecules were effective against HER2d16. Using T-DM1, we found that HER2d16 was only weakly impacted, while the growth of HER2-WT MM3MG were significantly suppressed (FIG. 6). Additionally, the use of Lapatinib only had a minor effect on the growth of our HER2d16 tumors (FIG. 7). These results demonstrate that HER2d16 may be resistant to these therapies, which we are currently exploring further.

Figure 8:
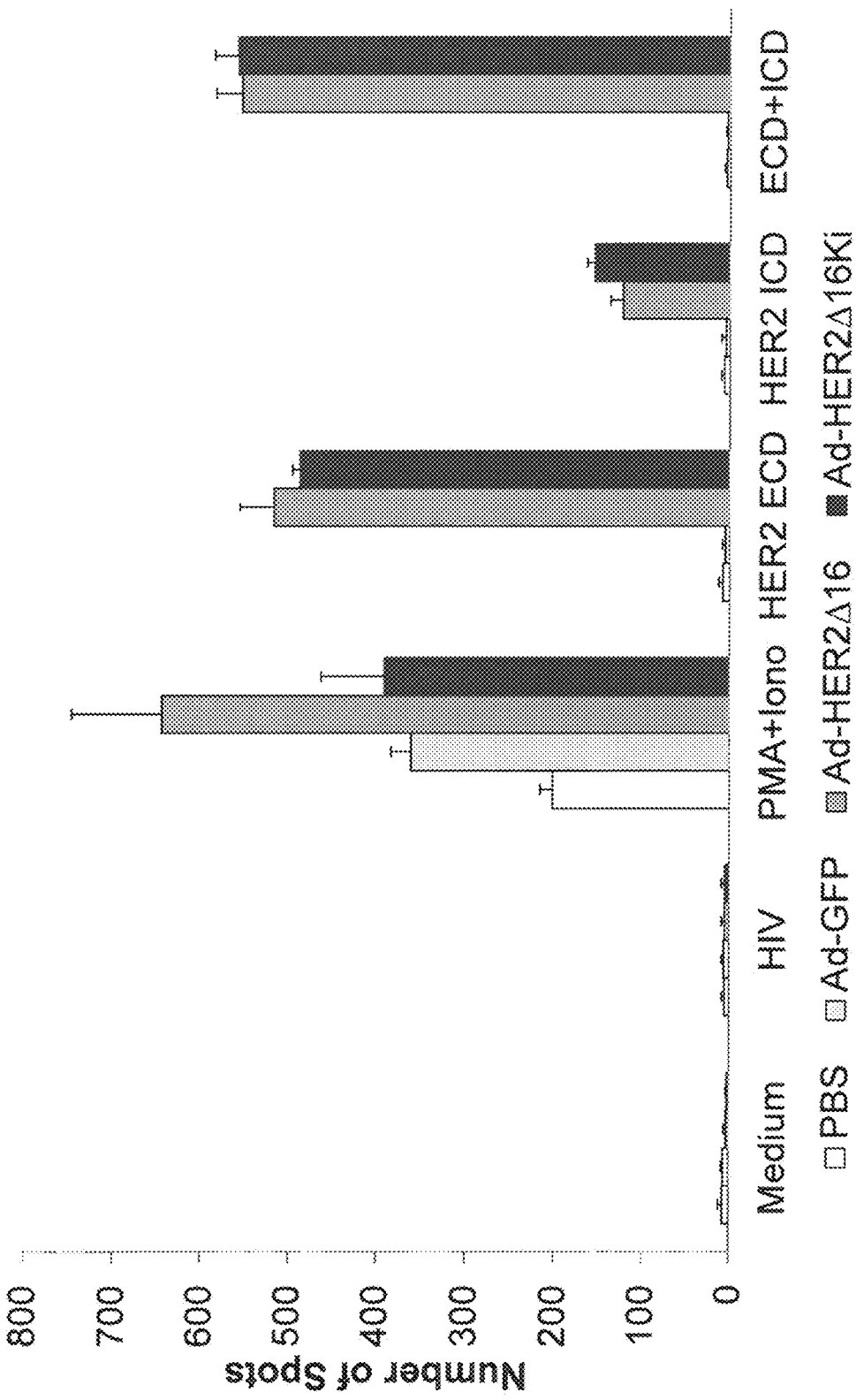
FIG. 8 is a graph showing that the adenoviral vaccines targeting HER2d16 elicit significant T-cell responses against HER2-specific epitopes. BALB/c mice were vaccinated using the indicated adenoviral vectors (2.6E10 viral particles per mouse via footpad) and sacrificed at 2 wpi. ELISPOT assays were then performed using 500 k splenocytes per well against the indicated antigen stimuli (N=5, bars represent SD).
Figure 9:
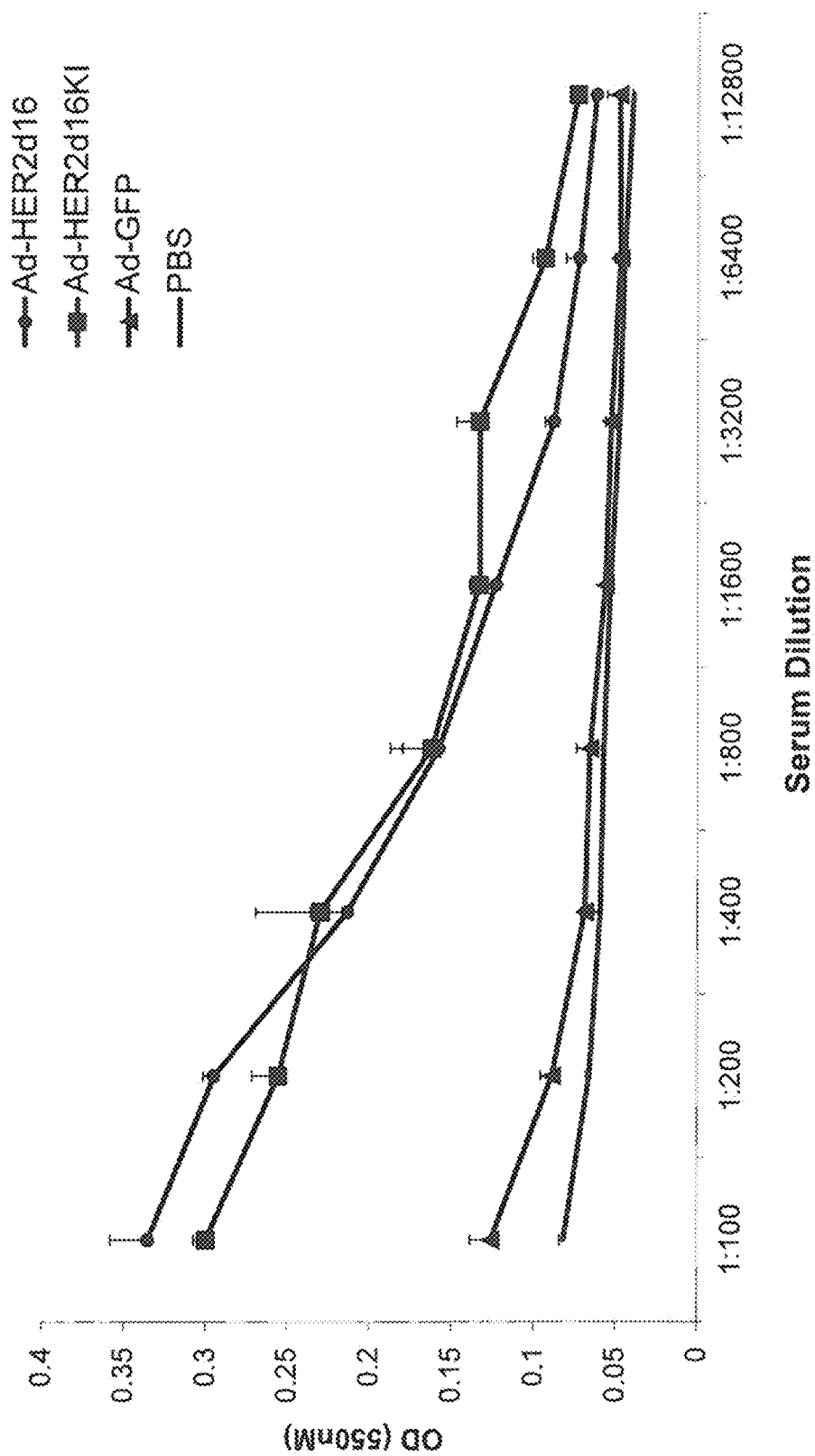
FIG. 9 is a graph showing that the adenoviral vaccines targeting HER2d16 elicit significant B-cell responses against HER2d16-specific epitopes. BALB/c mice were vaccinated using the indicated adenoviral vectors (2.6E10 vp per mouse via footpad) and sacrificed at 2 wpi. ELISA assays were then performed using HER2d16 expressing cell in a cell-based ELISA using an anti-mouse IgG-HRP secondary antibody (CST, 1:1000 dilution) to detect HER2d16-specific IgG antibodies. (N=5, bars represent SD).
Figure 10:
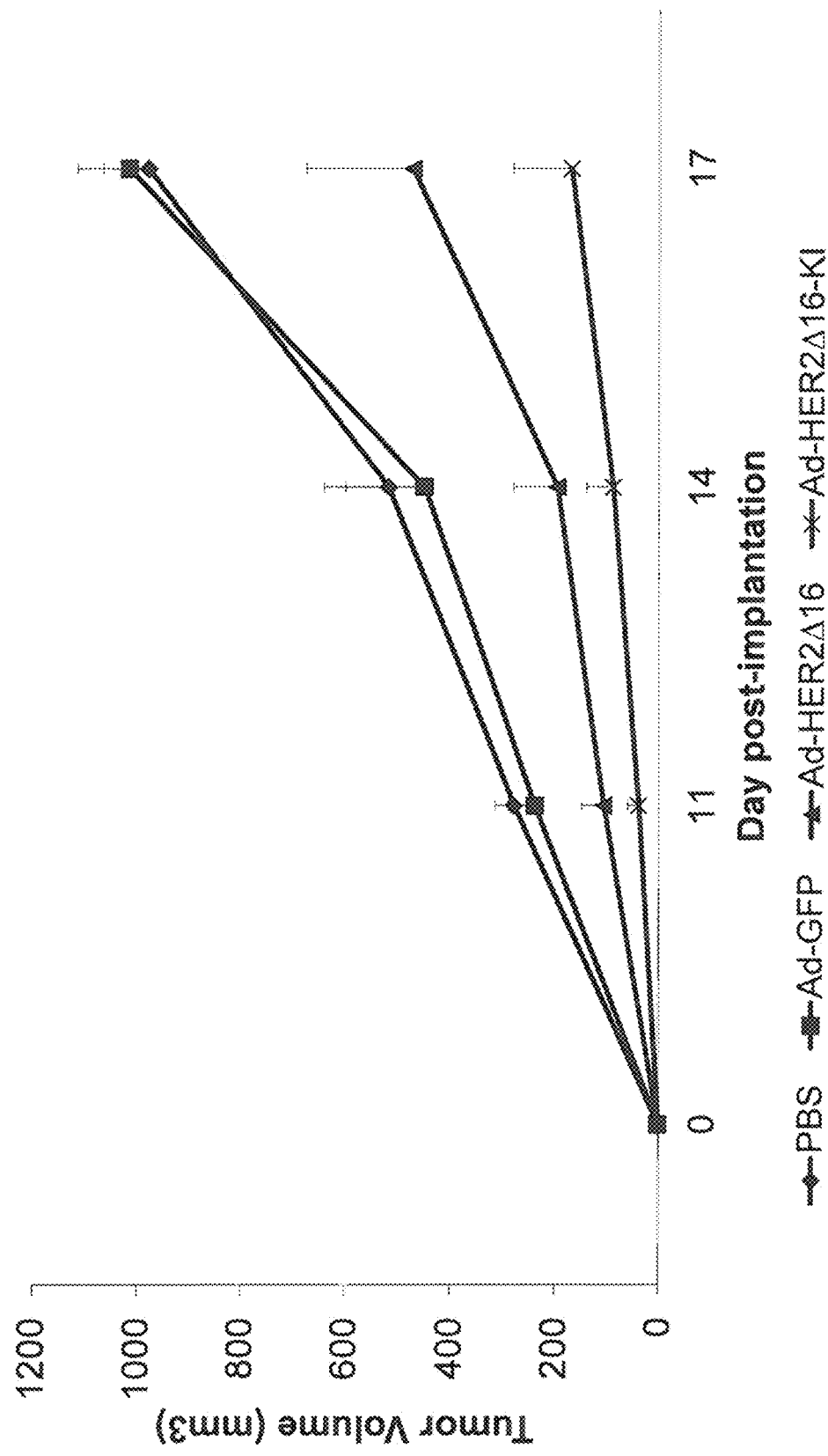
FIG. 10 is a graph showing that targeted vaccination against HER2d16 suppresses the growth of HER2d16 expressing cells. F1-HER2 Transgenic mice were implanted subcutaneously with MM3MG cells stably expressing the indicated genes (100,000 per mouse in PBS, indicated at day 0). These mice were then vaccinated 3 days post-implantation using the indicated adenoviral vectors (2.6E10 viral particles per mouse via footpad). Tumor growth was measured by calipers at the indicated days (N=5, bars represent SE).
Figure 11:
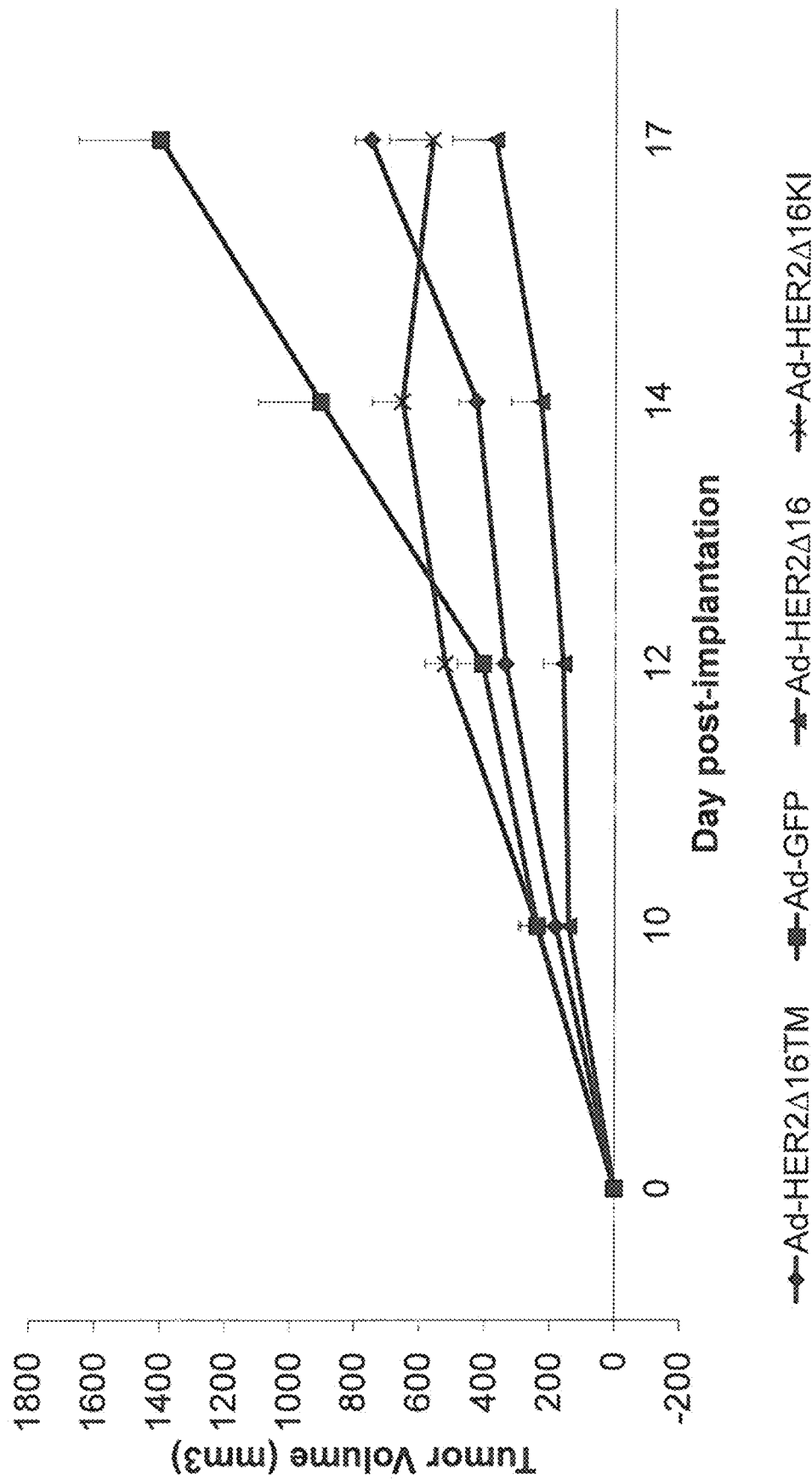
FIG. 11 is a graph showing that targeted vaccination against HER2d16 suppresses the growth of HER2d16 expressing cells. F1-HER2 Transgenic mice were implanted subcutaneously with MM3MG cells stably expressing the indicated genes (100,000 per mouse in PBS, indicated at day 0). These mice were then vaccinated 3 days post-implantation using the indicated adenoviral vectors (2.6E10 viral particles per mouse via footpad). Tumor growth was measured by calipers at the indicated days (N=5, bars represent SE).
Figure 12:
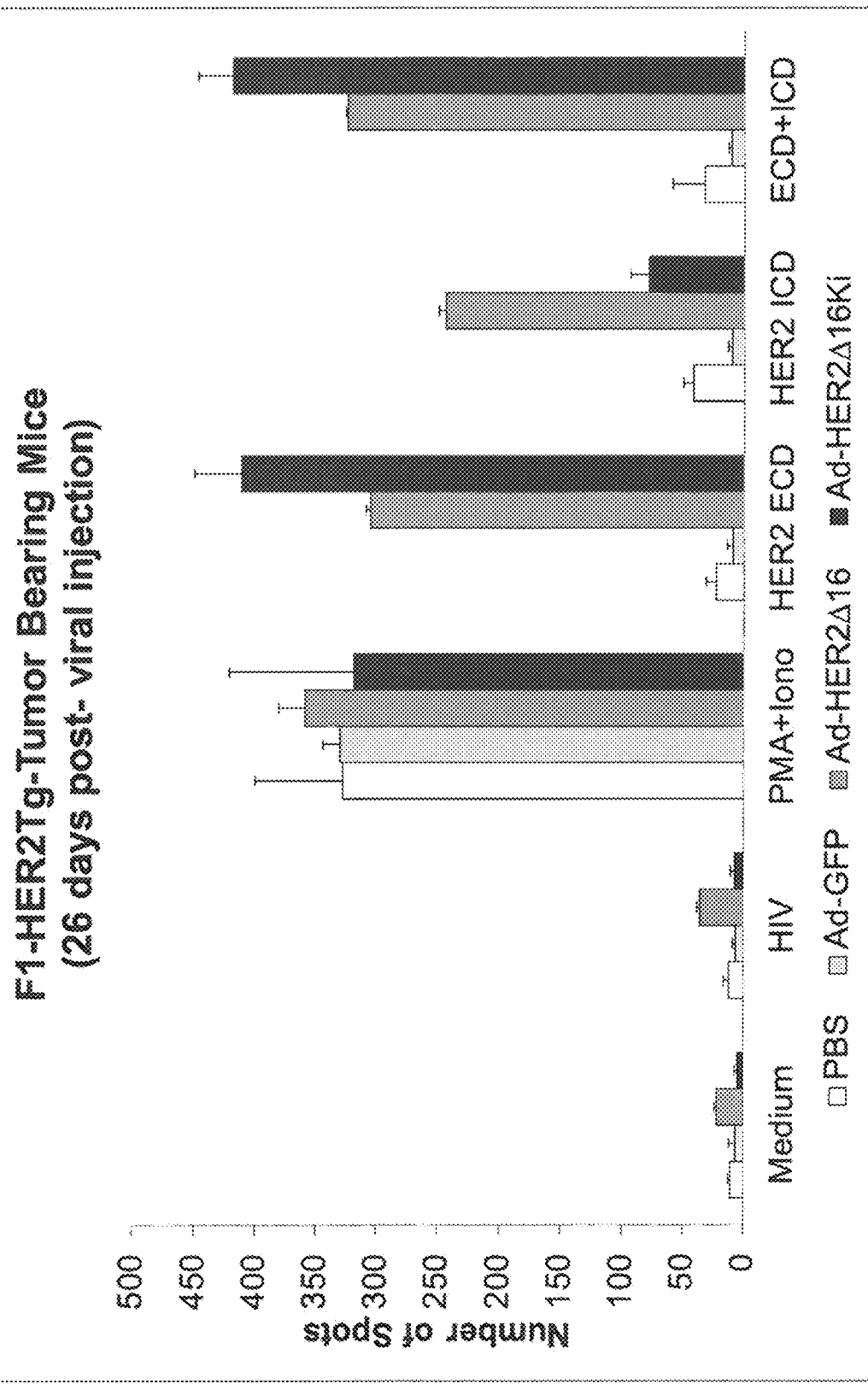
FIG. 12 is a graph showing that adenoviral vaccines targeting HER2d16 elicit T-cell responses against HER2-specific epitopes in tumor-bearing mice. F1-HER2 Transgenic mice were implanted subcutaneously with MM3MG cells stably expressing the indicated genes (100,000 per mouse in PBS, indicated at day 0). These mice were then vaccinated 3 days post-implantation using the indicated adenoviral vectors (2.6E10 viral particles per mouse via footpad). ELISPOT assays were then performed using 500 k splenocytes per well against the indicated antigen stimuli (N=5, bars represent SD).

While the standard-of-care targeted HER2 therapies proved ineffective against HER2d16 transformed cells, we wished to explore the capacity of a vaccine targeting this oncogenic isoform to elicit anti-tumor responses. As a preliminary step, we took advantage of our adenoviral vector platform, which we had previously demonstrated to be capable of eliciting strong anti-tumor immunity against multiple Tumor Associated Antigens, including HER2. Using this platform, we constructed adenoviral vectors encoding a full-length HER2d16 (HER2Δ16; SEQ ID NO: 2), an inactive version of the full-length HER2d16 gene (HER2Δ16Ki; SEQ ID NO: 4), and a truncated HER2d16 isoform (without an intracellular domain; HER2Δ16TM; SEQ ID NO: 6). After constructing and purifying these vectors, we ascertained their ability to elicit HER2d16-specific immunity in BALB/c and C57/BL6 animals. Using a HER2d16-specific ELISPOT assay, we determined that vaccination with HER2d16 or an inactive HER2d16 strongly elicited significant T-cell mediated immunity to HER2-specific epitopes (FIG. 8), while a HER2d16-specific ELISA assay demonstrated significant HER2d16 specific antibody responses (FIG. 9). Having thus demonstrated these vaccines were capable of eliciting B-cell and T-cell HER2d16-specific immunity, we next sought to determine if vaccination against this oncogenic isoform could significantly retard tumor growth. Having developed a HER2d16-transformed breast cancer line capable of growing in immunocompetent transgenic animals, we next implanted these cells into animals and tested if anti-HER2d16 responses elicited by vaccination could retard HER2d16-mediated growth. Our results from multiple experiments demonstrated that all HER2d16 vaccine formulations could significantly suppress HER2d16-mediated tumor growth (FIGS. 10 and 11) and that this was accompanied by significant induction of HER2d16-specific T-cell responses in Ad-HER2d16 vaccinated animals (FIG. 12). Notably, we found that Antibody responses to HER2d16 were elicited in all HER2d16 tumor-bearing animals (data not shown). As such, these results demonstrate that immunotherapeutic vaccination against an oncogenic isoform of HER2d16 can allow for strong HER2d16-specific immunity as well as significantly suppress the growth of HER2d16-driven breast cancers.

Figure 13:
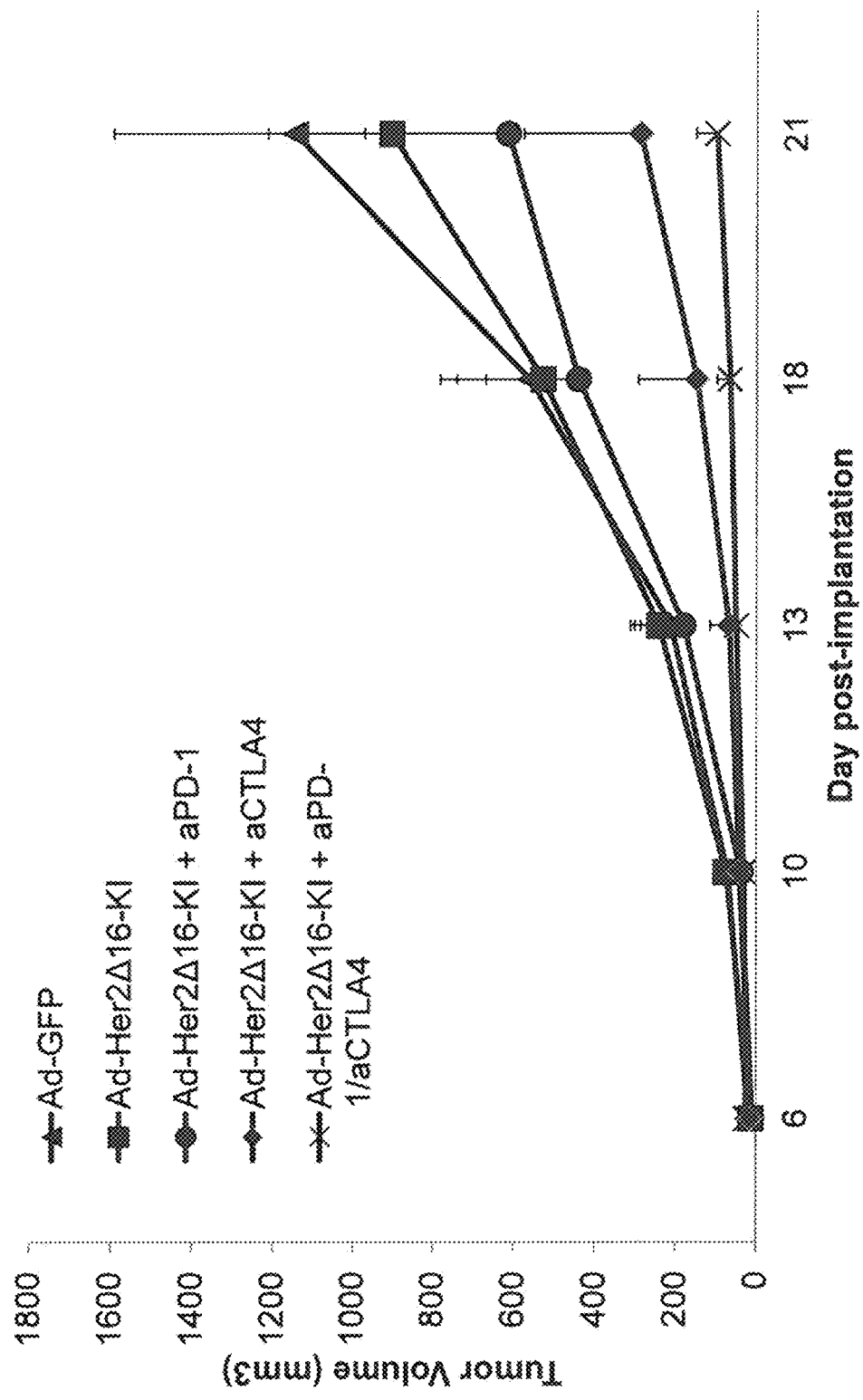
FIG. 13 is a graph showing that checkpoint inhibitors can enhance the anti-tumor effect of vaccination against HER2d16. F1-HER2 Transgenic mice were implanted subcutaneously with MM3MG cells stably expressing the indicated genes (100,000 per mouse in PBS, indicated at day 0). These mice were then vaccinated 3 days post-implantation using the indicated adenoviral vectors (2.6E10 viral particles per mouse via footpad). Anti-PD1 (RMP1-14; BioXCell) and Anti-CTLA4 (9D9; BioXCell) antibodies were administered on day 3 post-vaccination (200 μg/mouse) and then at weekly intervals (antibody only). Tumor growth was measured by calipers at the indicated days (N=5, bars represent SE).
Figure 14:
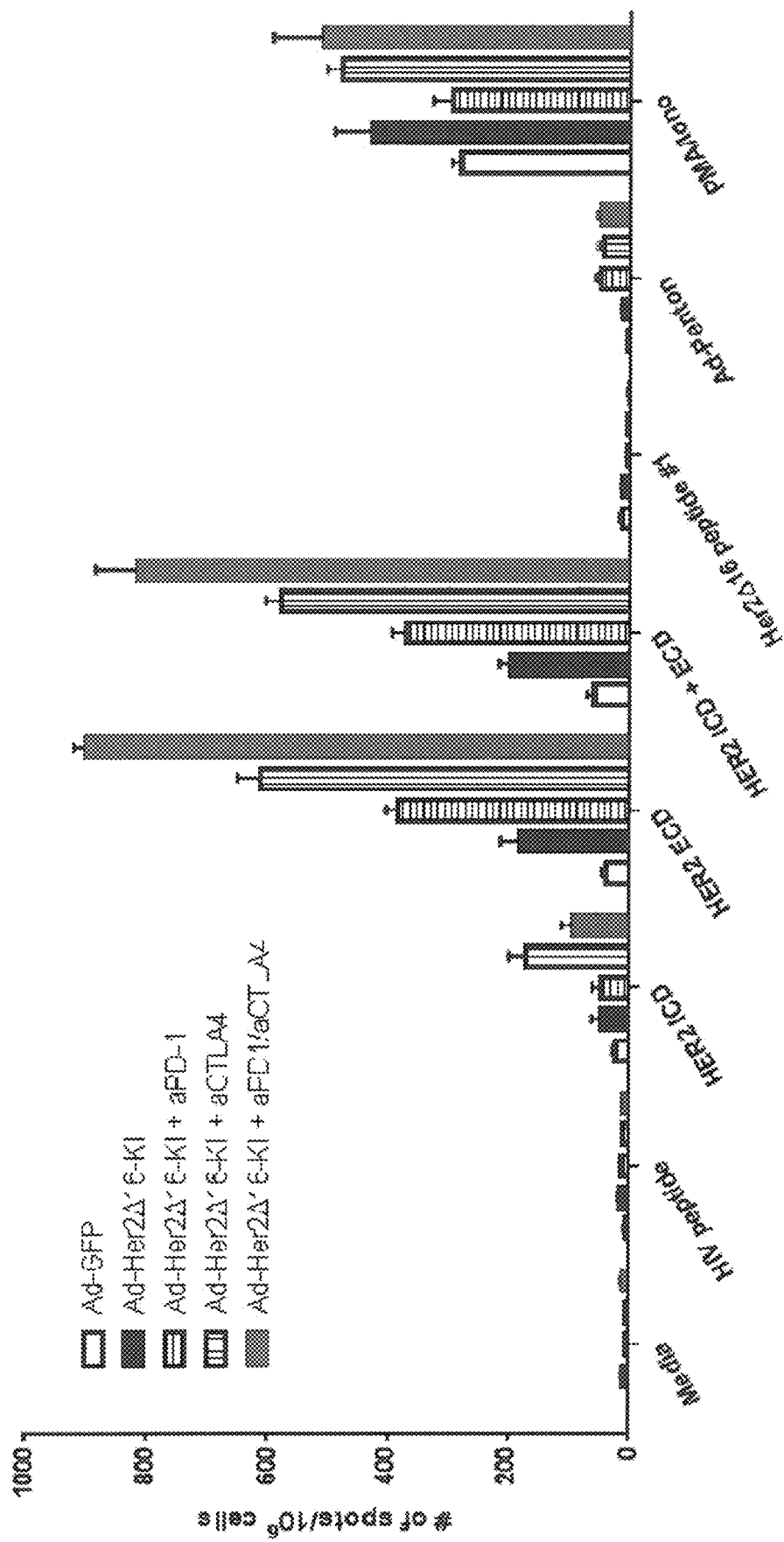
FIG. 14 is a graph showing that the adenoviral vaccines targeting HER2d16 elicit T-cell responses against HER2-specific epitopes in tumor-bearing mice which are significantly enhanced by checkpoint inhibitor antibodies. F1-HER2 Transgenic mice were implanted subcutaneously with MM3MG cells stably expressing the indicated genes (100,000 per mouse in PBS, indicated at day 0). These mice were then vaccinated 3 days post-implantation using the indicated adenoviral vectors (2.6E10 viral particles per mouse via footpad) along with checkpoint inhibitors (200 μg/mouse per week). ELISPOT assays were then performed using 500 k splenocytes per well against the indicated antigen stimuli (N=5, bars represent SD).

Finally, we wished to determine if our HER2d16 therapeutic vaccine could be enhanced by the use of checkpoint inhibitor immunomodulatory agents. Antibodies targeting CTLA4 and PD1 have demonstrate significant clinical efficacy in eliciting anti-tumor immunity, even without the benefit of targeted vaccination against tumor neoantigens. Using our MM3MG-HER2d16 model, we implanted tumor and vaccinated mice with or without CTLA4/PD1 blockade. We discovered that while our vaccine could retard tumor growth, both PD1 blockade and CTLA4 blockade enhanced Ad-HER2d16 anti-tumor effect. Furthermore, we found that a combination HER2d16 vaccine+checkpoint inhibitor allowed for highly significant tumor growth suppression, leading to tumor disappearance in 40% of animals tested (FIG. 13 and data not shown). Critically, we found that these inhibitors enhanced systemic T-cell responses to HER2d16 epitopes, strongly suggesting that this anti-tumor effect was mediated by HER2d16-specific T-cell mediated immunity (FIG. 14). As such, we expect that the use of checkpoint inhibitors in combination with our vaccine will allow for significant and sustained immune responses to critical oncogenic drivers, such as an oncogenic isoform of HER2 in HER2+ breast cancers.

1. Hartman, Z. C. et al. An adenoviral vaccine encoding full-length inactivated human Her2 exhibits potent immunogenicty and enhanced therapeutic efficacy without oncogenicity. *Clin. Cancer Res.* 16, 1466-1477 (2010).
2. Hartman, Z. C. et al. Growth of triple-negative breast cancer cells relies upon coordinate autocrine expression of the proinflammatory cytokines IL-6 and IL-8. *Cancer Res* 73, 3470-80 (2013).

3. Hartman, Z. C. et al. HER2 overexpression elicits a proinflammatory IL-6 autocrine signaling loop that is critical for tumorigenesis. *Cancer Res.* 71, 4380-4391 (2011).
4. Piechocki, M. P., Ho, Y. S., Pilon, S. & Wei, W. Z. Human ErbB-2 (Her-2) transgenic mice: a model system for testing Her-2 based vaccines *J. Immunol.* 171, 5787-5794 (2003).
5. Kershaw, M. H. et al. Gene-engineered T cells as a superior adjuvant therapy for metastatic cancer *J. Immunol.* 173, 2143-2150 (2004).
6. Mitra, D. et al. An oncogenic isoform of HER2 associated with locally disseminated breast cancer and trastuzumab resistance. *Mol Cancer Ther* 8, 2152-62 (2009).
7. Castiglioni, F. et al. Role of exon-16-deleted HER2 in breast carcinomas. *Endocr Relat Cancer* 13, 221-32 (2006).
8. Kwong, K. Y. & Hung, M. C. A novel splice variant of HER2 with increased transformation activity. *Mol Carcinog* 23, 62-8 (1998).
9. Castagnoli, L. et al. Activated d16HER2 homodimers and SRC kinase mediate optimal efficacy for trastuzumab. *Cancer Res* 74, 6248-59 (2014).

We claim:

1. A method of treating a HER2d16 containing cancer or precancer or of reducing the likelihood of the HER2d16 containing cancer developing resistance to a cancer therapeutic or prevention agent comprising administering a vaccine to a subject having the HER2d16 containing cancer or precancer, wherein the vaccine comprises a polynucleotide encoding a mutant HER2 polypeptide, wherein the HER2 polypeptide consists of SEQ ID NO: 4 or SEQ ID NO: 6, wherein administration of the vaccine to the subject treats the cancer or precancer, reduces the likelihood of the HER2d16 containing cancer or precancer developing resistance to the cancer therapeutic or prevention agent or reverses resistance of the cancer or precancer to the cancer therapeutic or prevention agent.

2. The method of claim 1, wherein the vaccine is administered concurrently with, before or after administration of the cancer therapeutic or prevention agent.

3. The method of claim 2, wherein the cancer therapeutic or prevention agent is an agent targeting HER2, HER1, estrogen receptor, or IGF1R.

4. The method of claim 1, wherein the vaccine is administered concurrently with, before or after administration of a checkpoint inhibitor immunomodulatory agent.

5. The method of claim 4, wherein the checkpoint inhibitor immunomodulatory agent is a CTLA-4 or PD1 antagonistic antibody.

6. The method of claim 1, wherein the cancer or precancer is selected from a breast, prostate, lung, ovarian, colon, rectal, pancreas, bladder, head and neck or liver cancer or precancer.

7. The method of claim 1, wherein the subject develops an immune response to HER2 after administration of the vaccine.

8. The method of claim 7, wherein the immune response comprises an antibody response or a T cell mediated response.

9. The method of claim 7, wherein the immune response includes at least one of antibody-dependent cellular cytotoxicity, polyclonal antibody response, complement dependent cellular cytotoxicity, cellular cytotoxicity, disruption of ligand binding, disruption of dimerization, mimicking ligand binding causing internalization of HER2, or degradation of HER2.

10. The method of claim 1, wherein administration of the vaccine results in a reduction of HER2 expression on cancer or precancer cells after administration of the vaccine as compared to a level of HER2 on the cells prior to vaccination.

11. The method of claim 1, wherein administration results in decreased tumor growth rate or decreased tumor size after administration as compared to prior to administration.

12. The method of claim 1, wherein the cancer therapeutic or prevention agent is selected from trastuzumab, lapatinib, cetuximab, pertuzumab and erlotinib.

\* \* \* \* \*